United States Patent [19]
dePinto

[11] Patent Number: 5,999,845
[45] Date of Patent: Dec. 7, 1999

[54] MUSCLE ARTIFACT NOISE DETECTOR FOR ECG SIGNALS

[75] Inventor: Victor M. dePinto, Kirkland, Wash.

[73] Assignee: Quinton Instrument Company, Bothell, Wash.

[21] Appl. No.: 09/081,950

[22] Filed: May 20, 1998

Related U.S. Application Data

[60] Provisional application No. 60/047,254, May 21, 1997.

[51] Int. Cl.[6] .................................................. A61B 5/0402
[52] U.S. Cl. ............................................ 600/509; 128/901
[58] Field of Search ............................ 128/901; 600/508, 600/509, 521, 522

[56] References Cited

U.S. PATENT DOCUMENTS 3,903,874   9/1975   Shakespeare .
4,887,609  12/1989   Cole, Jr. .

*Primary Examiner*—William E. Kamm
*Assistant Examiner*—George R. Evanisko
*Attorney, Agent, or Firm*—Graybeal Jackson Haley LLP

[57] ABSTRACT

A filter system for detecting and removing small amplitude, high frequency signals such as muscle artifact signals is provided. One form of the system includes a baseline wander filter, high and low pass filters, an adaptive line noise canceler and various noise detectors to identify, signal and remove muscle artifact or loose electrode signal contamination from an ECG signal wherein the ECG signal is conditioned to remove various portions of the ECG signal, such as the QRS portion of the ECG signal, prior to processing in various noise detectors while minimizing the signal conditioning effect of the filters on the ECG signal and while further providing the operator with the ability to manually or automatically activate the filters and to indicate the status of the filters on a printout or display.

19 Claims, 16 Drawing Sheets

| COEFFICIENT | VALUE |
|---|---|
| 1A1 | 0.504559620902 |
| 1B1 | −1.0 |
| 1C | 0.752279810451 |
| 2A1 | 1.281243390985 |
| 2A2 | −0.527704100019 |
| 2B1 | −1.940533108119 |
| 2B2 | 1.0 |
| 2C | 0.712834384062 |
| 3A1 | 1.610104519260 |
| 3A2 | −0.866248394746 |
| 3B1 | −1.864510411616 |
| 3B2 | 1.0 |
| 3C | 0.899558428813 |

*figure 5*

MUSCLE ARTIFACT NOISE DETECTOR FOR ECG SIGNALS

CROSS-REFERENCE TO RELATED APPLICATIONS

This is a continuing application based on priority of U.S. Provisional Application Ser. No. 60/047,254 filed May 21, 1997.

FIELD OF THE INVENTION

The instant invention relates to a wide band noise detector and/or filter for detecting the presence of various types of interference which are typically present in a physiological signal acquired by monitoring or acquisition device such as an ECG machine, and more particularly to a wide band noise filter and detector which estimates noise levels, compares these levels to threshold values and reports the resulting noise status to cancellation filters and the user to signal the presence and/or remove the wide band noise in an ECG signal wherein the wide band noise is caused by conditions such as muscle artifact electrode movement during acquisition of the ECG signal.

BACKGROUND OF THE INVENTION

A common problem in electrocardiography monitoring or acquisition is the contamination of the ECG signal with power line noise, wideband noise, or baseline wander. These distortions render the electrocardiogram difficult to read.

Power line noise is typically caused by environmental interference with the ECG device at about 50 Hz or 60 Hz. A common solution to correct the ECG for power line noise has been to pass the signal through a bandstop filter which rejects signal components at the power line frequency. However this filter has the disadvantage that it can cause ringing in the vicinity of the QRS complex of the ECG signal. Another solution is to employ an adaptive noise canceler to reduce or eliminate power line interference. This solution is less likely to cause objectionable ringing.

A common solution to correct the ECG for the wideband noise, which may be caused by muscle artifact or electrode movement, has been to pass the ECG signal through a low pass filter having a low cut-off frequency, typically about 25 Hz. Since wideband noise signals typically have significant energy at frequencies higher than 25 Hz, the low pass filter effectively reduces the muscle artifact signal. However, the use of a low pass filter has the disadvantage of also reducing the amplitude of the QRS complex because the high frequency components of the ECG signal which are necessary to describe the relatively high peaks of the QRS signal are also removed as the ECG signal passes through the low pass filter. An example of an approach to filtering muscle artifact in an ECG signal is disclosed in U.S. Pat. No. 5,259,387 granted to dePinto and owned by the assignee of the present invention.

Baseline wander is typically caused by interactions between the skin of the patient and the electrode where acids naturally present in the skin of the patient react with metals in the electrode to create an electrolytic reaction on the skin of the patient. This electrolytic reaction, which is similar to the reaction in a battery, provides a relatively constant long term or DC signal which varies slowly over time, producing a low frequency interfering signal superimposed on the electrocardiogram.

One common solution to overcome or minimize the problem of baseline wander is to abrasively remove the top layer of the skin of the patient. Another solution to the problem of baseline wander is to convert the ECG signal to a digital signal on a processing device by creating a cubic spline which passes through the P-R segment of every beat. The cubic spline is then used to determine an offset to be added to the ECG signal to cancel or adjust for the baseline wander. Yet another solution to this problem is to use a high pass filter to remove the slowly varying signals such as baseline wander. Ideally, these filters pass all frequencies above about 0.5 Hz, since baseline wander typically occurs with frequencies below this level and the energy in an ECG signal is primarily above this frequency.

Although the filtering methods described above are effective in reducing or eliminating interfering signals, these filters can also cause a certain amount of distortion of the ECG signal. Even though the magnitude of this distortion may not be sufficient to cause serious problems, it would be preferable to employ the filters only when excessive noise is present and to turn them off at other times. Furthermore, it is preferable to eliminate the source of noise, for example poor electrode preparation or strong electric fields in the vicinity of the patient, instead of turning on a filter.

What is needed is an automatic method of detecting interfering signals and notifying the user. The user may then take corrective action or turn on the appropriate filters. Filters may also be controlled by the automatic noise detection system in such a way as to be turned on when noise is present and turned off when noise levels are low while providing the user with an indication that the filters are on or off and allowing the user to manually override the automatic activation or deactivation of the filters.

SUMMARY OF THE INVENTION

In the present invention, a noise detector is used to detect each of the three basic types of noise: Power line noise, wideband noise caused by muscle tremor or mechanical vibration of electrodes, and baseline wander. The basic detection scheme consists of estimating noise levels, comparing these levels to their respective noise threshold values and then reporting the resulting noise statuses to various signals to notify the user of the presence of detected noise and/or passing the signals to various filters.

The comparison of the noise levels to the respective threshold values in this invention is preferably accomplished by comparing the noise detector's output to a threshold level representing the maximum tolerable noise level.

The line noise detection component of the noise detector of the present invention preferably includes a frequency selective incoherent demodulator which measures the amplitude of the signals within its passband. The QRS complex is blanked before being passed to the line noise detector, because the QRS complex contains high frequency energy which might be detected as line noise. In the present invention, the line frequencies preferably must be within about ±0.2 Hz (50 Hz±0.2 Hz and 60 Hz±0.2 Hz) in order to be detected. The first comparison performed by the comparators is with a line threshold equivalent to about 15 microvolts at the input. The second comparison performed by the comparators is with 0.2 times the wideband level output. This value serves as a ratio factor so that, not only does the line level have to exceed the line threshold, it must also be greater than a predetermined value times the output of the wideband noise detector.

The wideband noise detector portion of the present invention preferably computes a running average of the squared sample values of the ECG signal. The QRS complex is blanked before being passed to the wideband detector because the QRS complex contains high frequency energy which might be detected as wideband noise. The signal also passes through a line noise canceler before reaching the wideband noise detector, because the wideband noise detector of the preferred embodiment cannot distinguish between line frequency interference and wideband noise such as muscle artifact.

The output of the wideband noise detector is presented to a comparator which generates a Boolean signal when the amplitude of the wideband noise exceeds a predetermined threshold.

The baseline wander detector portion of the present invention utilizes an input which consists of baseline estimate values from the baseline wander filter. The basic premise of the baseline wander detector is that if the baseline wander level is at or above the threshold, then the existence of baseline wander is reported. If the baseline wander noise is below the threshold level for the current sample and the baseline wander noise has been absent for a predetermined number of samples, then the absence of baseline wander is reported. In one form of the present invention a delay of about eight seconds for eight channels of data may be used. In a more preferred form of the present invention a delay of about four seconds for eight channels of data is preferably used to minimize toggling of the noise status indicator.

It is therefore an object of the instant invention to provide a detection and filtering system for detecting and filtering line noise, baseline wander, and wideband noise such as muscle artifact signals to maximize the filtering of noise signals during the part of the ECG signal where the noise is most commonly present, yet which passes the ECG signal with a minimum of distortion due to filtering when various noise signals are not present.

It is a further object of the instant invention to provide a detection and filtering system which may be readily implemented on a digital processing system.

It is a further object of the instant invention to provide a detection and filter system which may be easily implemented with other detection and/or filter systems in an ECG monitoring system.

Furthermore, it is an object of the instant invention to provide a detection and filtering system which is reliable and relatively simple and easy to make and use.

These and other objects of the instant invention will become clear from the description contained herein and more particularly with reference to the following detailed description where like elements are referred to by like reference numbers.

BRIEF DESCRIPTION OF THE DRAWINGS

FIG. 5 is a table of coefficients used in the realization of the high pass filter of FIG. 4;

DETAILED DESCRIPTION OF THE INVENTION

Figure 1:
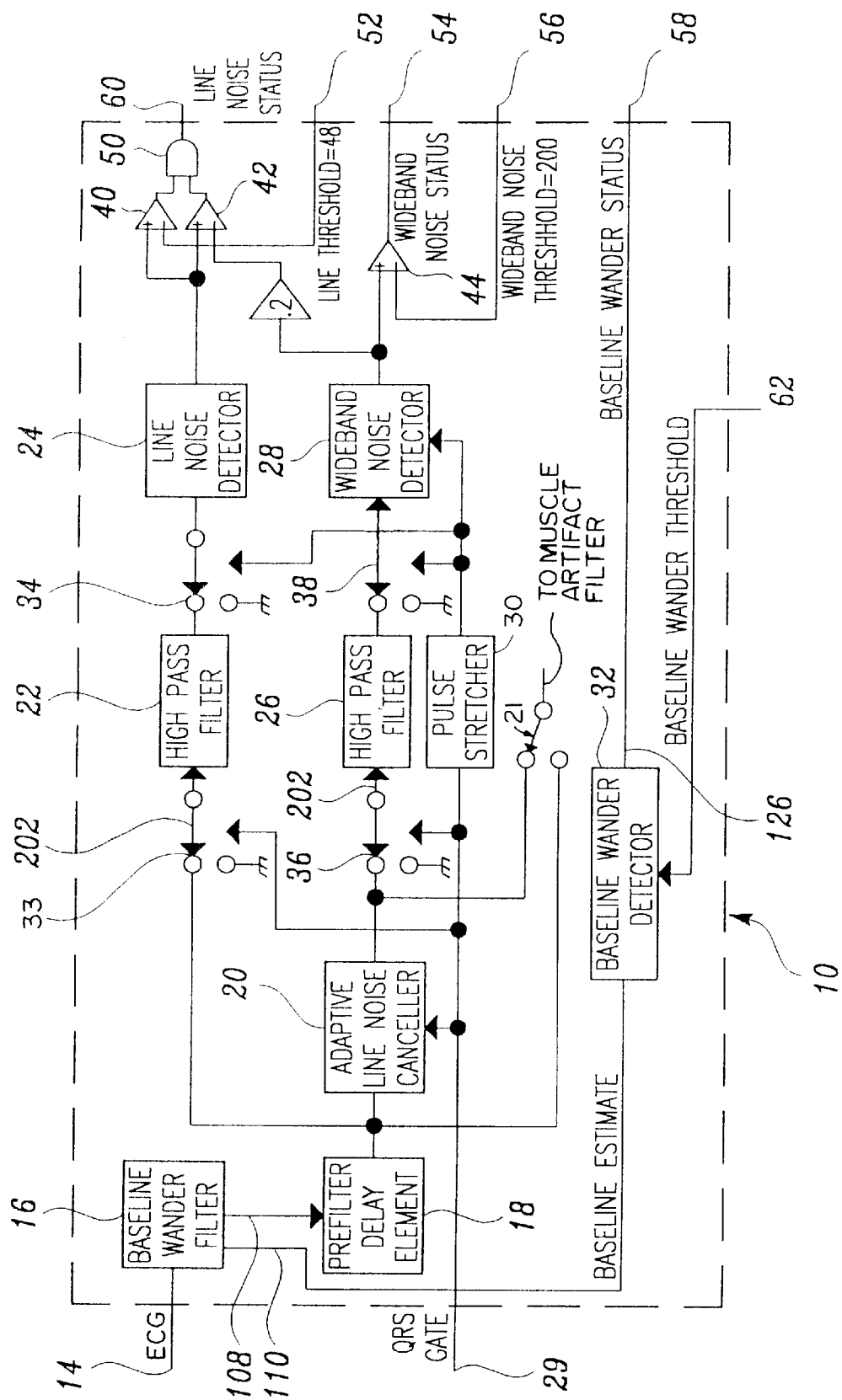
FIG. 1 is a block diagram of the preferred form of the ECG noise detection system of the present invention.

As shown in FIG. 1, the noise detection system of the present invention is generally labeled as element 10. The noise detection system 10 is shown in a block diagram of the preferred form of its basic elements. An analog ECG signal is received from each of a series of electrodes placed on a patient (not shown) and is first converted to a digital signal through an A to D converter such as is common in the art. The digitized ECG signals 14 from the electrodes are thereafter combined in a manner well known in the art in order to form signals called leads. The noise detection system 10 of the preferred embodiment is capable of detecting noise in a single lead at a time. A typical electrocardiograph produces 12 leads. Therefore, a 12-lead electrocardiograph would require 12 noise detection systems in order to detect noise in all 12 leads.

Throughout this disclosure reference will be made to parallel processing in various elements of the noise detection system 10 of either all or selected portions of the ECG signals. By parallel processing it is meant that a series of input signals produce a corresponding series of output signals. This parallel processing is preferably accomplished by sequential processing by a single digital device such as a microprocessor of the individual input signals during the interval between the collection of samples so that a virtual or apparent parallel processing is performed. Of course, it is anticipated that actual parallel processing of the ECG signals could be done by parallel hardware where the input signals are each processed by their own processing hardware. These individual pieces of processing hardware could then include individual microprocessors for each signal.

The noise detection system of the present invention basically includes the steps of estimating noise levels, comparing the estimated noise levels to their respective noise threshold values and reporting the resulting noise statuses to the outside world.

As shown in FIG. 1, one of the ECG lead signals 14 from the patient is applied to and input to the baseline wander filter 16. The ECG signal is subsequently passed to the line noise detector 24, the wideband noise detector 28 and the baseline wander detector 32. However, the signal passes through other processing elements before reaching these detectors as described below.

Figure 2A:
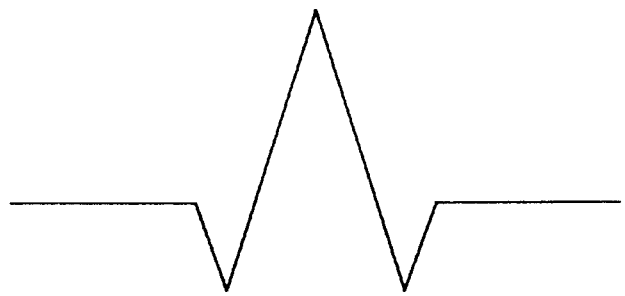
FIG. 2A is a graph illustrating the typical ECG signal showing the QRS complex.
Figure 2B:
FIG. 2B is a graph illustrating the relative timing of the QRS gate pulse of the present invention.
Figure 2C:
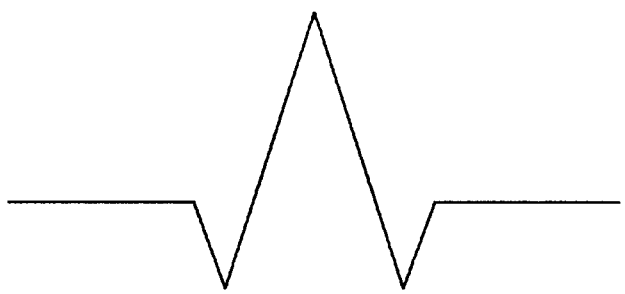
FIG. 2C is a graph illustrating the relative timing of the delayed ECG signal as a result of the prefilter delay element of the present invention.
Figure 2D:
FIG. 2D is a graph illustrating the relative timing of the stretched QRS gate pulse.

FIG. 2A shows an example of the QRS complex of the ECG signal at the input 14 to the noise detection system 10. FIG. 2B shows an example of the QRS gate pulse at the input 29 of the noise detection system 10, coinciding with and blanking the QRS complex. FIG. 2C shows the relative delay of the QRS complex at the output of the prefilter delay element 18. FIG. 2D shows the stretched QRS gate pulse at the output of the pulse stretcher 30. As shown in FIGS. 2A–D, the onset of the stretched pulse is preferably coincident with that of the unstretched pulse, but the stretched pulse preferably ends approximately 52 milliseconds after the end of the unstretched pulse. Note, also, that the stretched pulse preferably begins before the delayed QRS complex and ends after the end of the delayed QRS complex.

Figure 3:
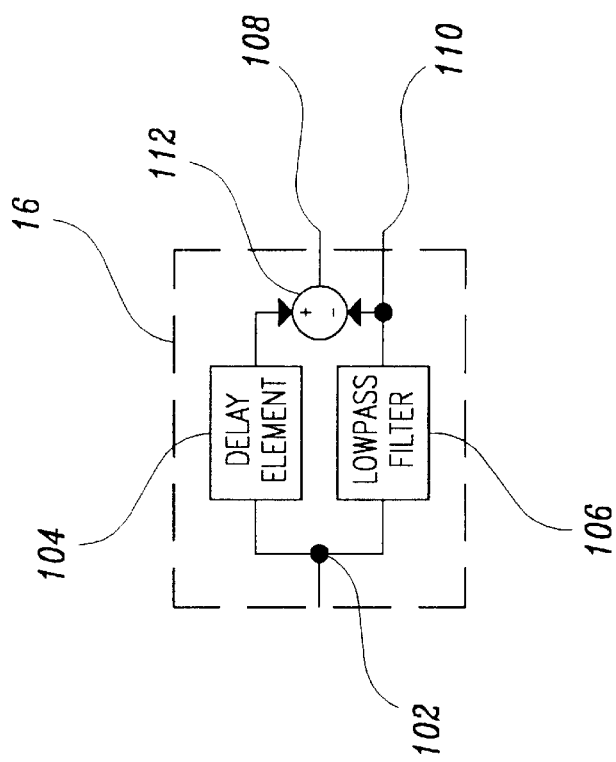
FIG. 3 is a block diagram of the preferred form of the baseline wander filter of the present invention as shown from the block diagram of FIG. 1.

The preferred form of the baseline wander filter 16 is shown in further detail in FIG. 3. An input of the digitized ECG signal 14 is presented to the baseline wander filter at an input 102 where it is split and simultaneously presented to a delay element 104 and a low pass filter 106. The delay element 104 electronically delays the ECG signal 14 from the input 102 for a time which is equal to the processing time of the low pass filter 106 by techniques which are well known in the art. The low pass filter 106 is preferably an infinite impulse response linear phase type of low pass filter whose cutoff frequency is about 0.2789 Hz. The signal outputs from both the delay element 104 and the low pass filter 106 are then simultaneously presented to a summer 112. The summer 112 subtracts the signal output of the low pass filter 106 from the signal output of the delay element 104. The baseline wander filter of the preferred form of the present invention is essentially a linear phase high pass filter. The signal output of the summer 112 is presented as the ECG output 108 so that the signal which is output from the ECG output 108 is the high pass filter output of the baseline wander filter 16. In the preferred form of the embodiment described here, this high pass filter preferably has a cutoff frequency of about 0.5 Hz. The cutoff frequency of this high pass filter can be altered, if desired, by altering the cutoff frequency of the low pass filter 106 component of the baseline wander filter 16. The signal which is output from the low pass filter 106 is basically an estimate of the baseline wander of the ECG signal. The baseline wander in an ECG signal is typically caused by the chemical interaction of the electrodes and the skin of the patient and is not part of the actual ECG signal generated by the heart. Because the heart-generated ECG signal contains frequencies mostly above 0.5 Hz, and the baseline wander portion of the acquired signal consists mostly of lower frequencies, the low pass filter 106 passes the baseline wander component of the signal and rejects the heart-generated ECG signal. Therefore, the output of the low pass filter 106 can be regarded as an estimate of the amount of baseline wander present in ECG signal 14. This baseline wander estimate is subtracted from the ECG signal in the summer 112 in order to obtain an ECG signal at the ECG output 108 which is free of baseline wander.

Another preferred form of the baseline wander filter 16 is described in more detail in U.S. Pat. No. 5,269,313 which is commonly owned by the assignee of the present invention. Although the baseline wander filter described herein is the preferred embodiment, there are other techniques which may also yield satisfactory results.

The baseline wander filter 16 of the present invention has an added feature which is not included in the filter described in U.S. Pat. No. 5,269,313. As shown in FIGS. 1 and 3, the output of the low pass filter 106 includes a pair of output signals, the baseline wander estimate output signal 110 as well as the ECG output 108. The signal shown as the baseline wander estimate output 110 is the output of the low pass filter 106 and is an estimate of the amount of baseline wander in the ECG signal. The baseline wander estimate output 110 is used by the baseline wander detector 32 to determine if the ECG signal has an excessive amount of baseline wander as described more fully below.

As shown in FIG. 1, the noise detection system of the present invention preferably includes a delay element 18 which electronically delays the ECG signal at the ECG output 108 of the baseline wander filter 16 for a predetermined time period. In the preferred form of the present invention, the delay may be about 46 milliseconds. The delay element 18 of the preferred embodiment is preferably a digital delay such as is common in the art whereby input digital signals are electronically delayed for a prespecified number of unit delay periods. Typically, such delay devices include electronic memory which stores sequential portions of the input signal for the desired delay time. The delayed signal at the output of the delay element 18 is then passed to various other elements of noise detection system 10 as shown in FIG. 1 and described below.

Figure 7:
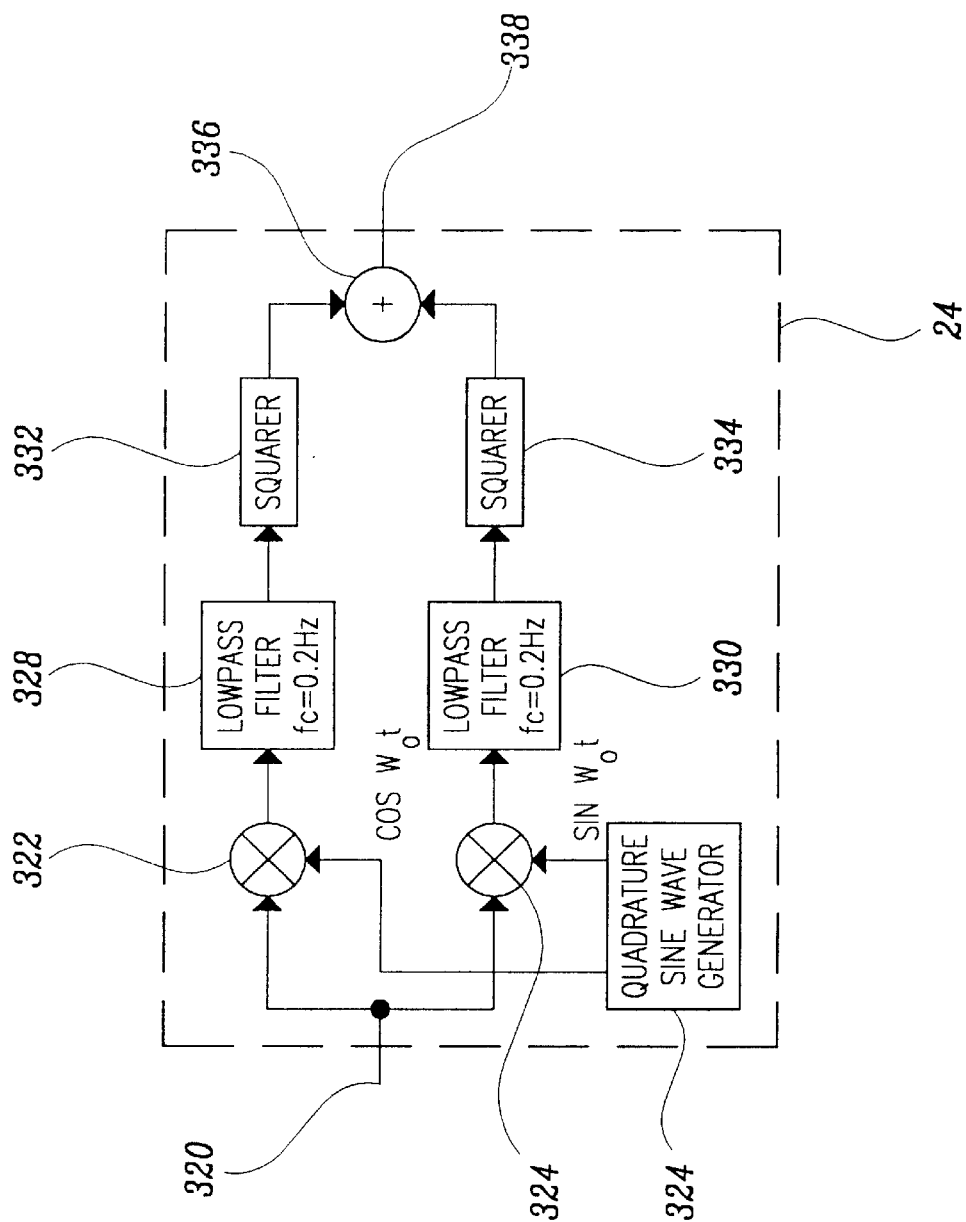
FIG. 7 is a block diagram of the preferred form of the line noise detector of the present invention as shown from the block diagram of FIG. 1.

The ECG signal must pass through the prefilter delay element 18 before reaching the input of the line noise detector 24, the wideband noise detector 28 and the baseline wander detector 32. The ECG signal must also pass through the high pass filter 22, as described more fully below, to reach the line noise detector 24. As shown in FIG. 7, the line noise detector 24 is preferably an incoherent demodulator, which measures the amplitude of the signal component at the typical power line frequencies. In the preferred embodiment, this is usually at about 50 or 60 Hz. The QRS complex of the ECG signal normally also has significant energy at the power line frequency. Because it is desired to measure only the 50 or 60 Hz contamination caused by external sources, the QRS complex is preferably blanked; i.e., removed from the ECG signal before it reaches the line noise detector 24. This is accomplished with the use of a QRS gate which preferably is a logic signal presented to the noise detection system at the input 29 as shown in FIG. 1. The QRS gate is preferably high (true) during the QRS complex of the ECG signal. The QRS gate controls the switch 33 and the switch 34 in such a way as to replace the ECG signal with zero (ground) for a period beginning just before the onset of the QRS complex and ending just after the QRS complex as shown in FIG. 2B. The other portions of the ECG signal pass through the switch 33 and the switch 34 normally. The prefilter delay element 18 of the preferred embodiment preferably delays the ECG signal by a predetermined amount which is approximately 46 milliseconds or about 23 samples in the preferred form of the present embodiment so that the QRS gate signal grounds the ECG signal at the switch 33 and also at the switch 34 prior to the onset of the QRS complex at the output of the prefilter delay element 18, thus preventing the QRS complex from reaching the line noise detector 24. The high pass filter 22 is placed in the signal path in order to remove transient effects such as step changes in the baseline of the ECG signal due to the operation of the switch 33. The pulse stretcher 30 further increases the duration of the QRS gate signal. When the QRS gate signal goes high, the output signal of the pulse stretcher 30 goes high immediately. However, the output signal of the pulse stretcher 30 also goes low at a slower rate than the QRS gate signal. In the preferred form of the present invention, the pulse stretcher 30 goes low about 52 milliseconds after the QRS gate signal goes low. This delays the restoration of the ECG signal at the switch 34 until after the QRS complex and also after the high pass filter 22 stops ringing in response to the operation of the switch 33. Therefore, the signal reaching the input of the line noise detector 24 is a high pass filtered ECG signal with the QRS complex removed, and the output of the line noise detector 24 is an estimate of the amount of line frequency energy. This line frequency energy is usually at a frequency of 50 Hz or 60 Hz in the ECG signal.

In the preferred embodiment, the pulse stretcher 30 is implemented on a programmable digital computer. The preferred C language source code for pulse stretcher 30 is shown below. The stretched QRS gate pulse begins at the same time as the QRS gate, but is extended by 26 samples. This pulse is high whenever qrs_blank_ctr is nonzero.

If (QRS_gateB)

qrs_blank_ctr = 26;

Else if (qrs_blank_ctr > 0)

−−qrs_blank_ctr;

stretched_QRS_gate = (qrs_blank_ctr > 0)

Figure 4:
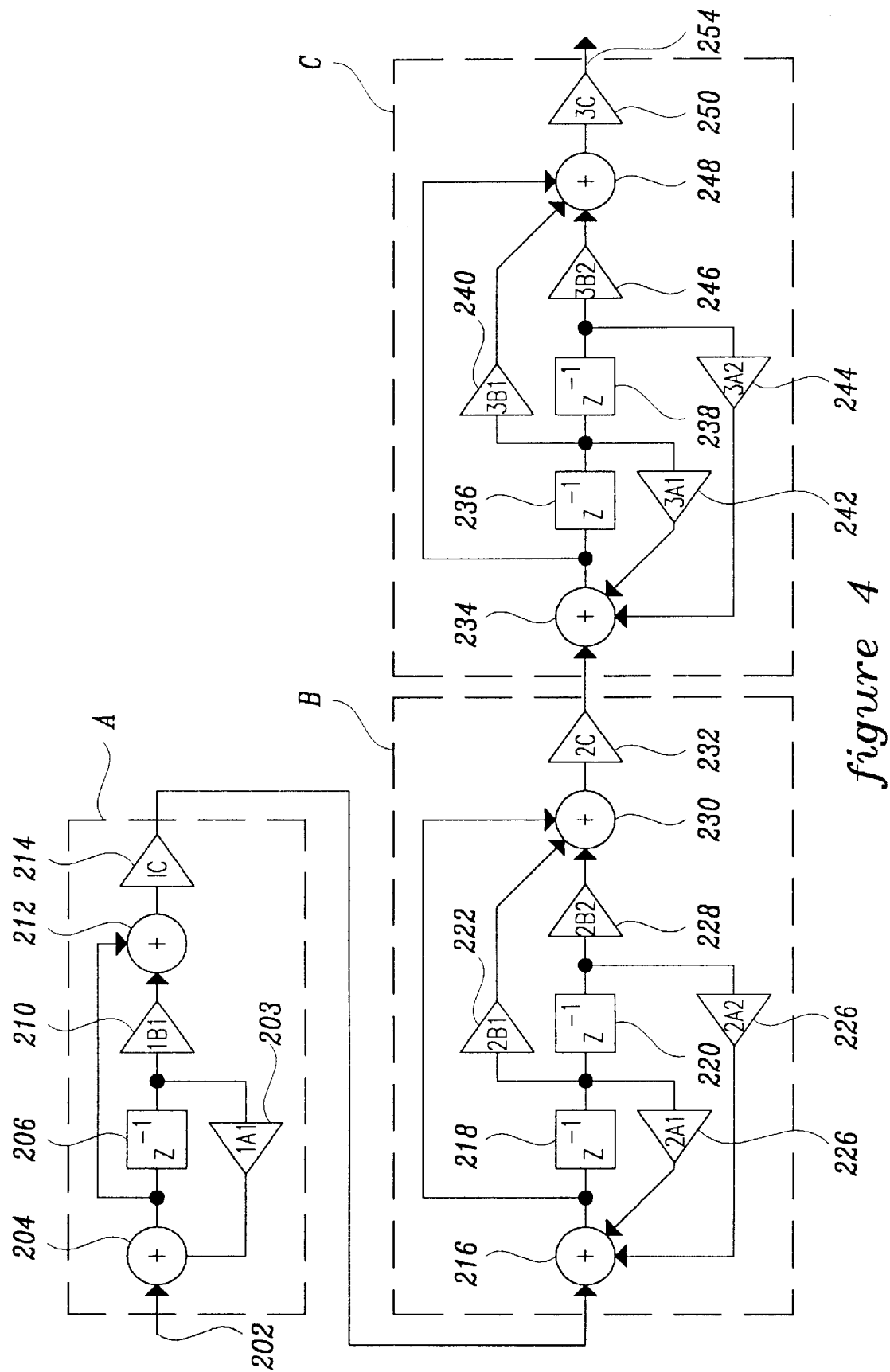
FIG. 4 is a block diagram of the high pass filter of the preferred form of the present invention as shown from the block diagram of FIG. 1.
Figure 6:
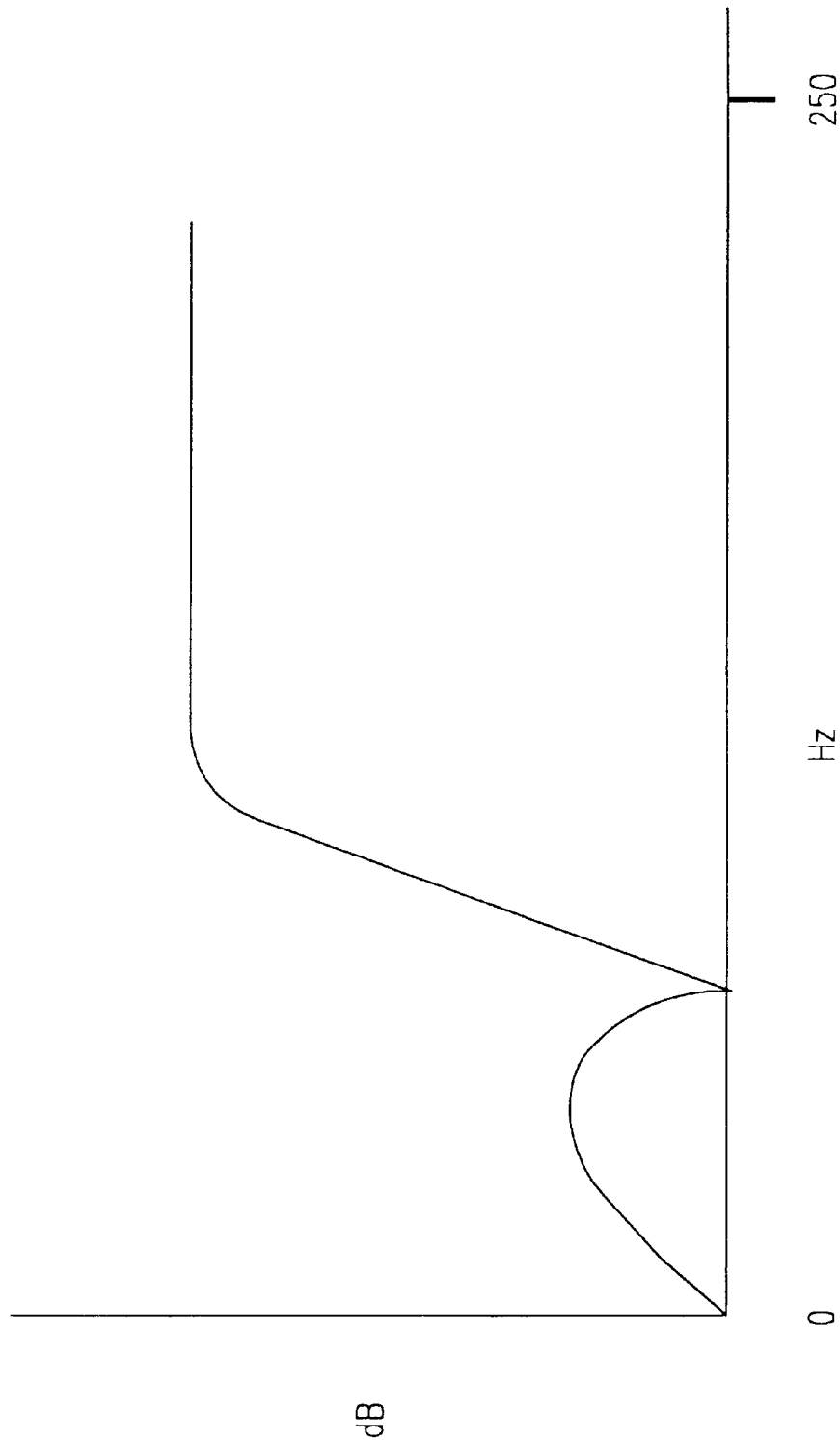
FIG. 6 is a frequency response plot of the high pass filter of FIG. 4.

As shown in FIG. 1, the high pass filter 22 receives the delayed signal from the delay element 18 via the switch 33. In the preferred form of the present invention, the high pass filter 22 is an elliptic filter having a cutoff frequency of about 50 Hz. It is preferably a fifth order infinite impulse response (IIR) filter and is realized in three stages—one first order stage followed by two second order stages. The three stages of realization for the preferred form of the high pass filter 22 are shown in FIG. 4. Section A of FIG. 4 shows the first order stage A. Section B of FIG. 4 shows the second order stage B. Section C of FIG. 4 shows the second order stage C. Although a filter of this type could be realized as a single fifth order stage, it is more preferable to divide it into first and second order stages as in this preferred embodiment. This is done because a realization consisting of first and second order stages requires less arithmetic precision and, therefore, can be executed more economically by a computer. A high pass filter 22 suitable for this application may also be constructed by using an finite impulse response (FIR) implementation. FIG. 6 shows an example of the frequency response plot of the preferred form of the high pass filter 22.

Referring to FIG. 4, the ECG signal which is presented to the high pass filter 22 as input signal 202 is immediately passed to the summer 204. At the summer 204, the input signal 202 has the output of the gain block 208 added to it as will be described hereafter. The output signal of the summer 204 is simultaneously presented to the unit delay 206 and to the summer 212.

The delay 206 as well as the delays 218, 220, 236 and 238 provide a unit delay for the signal presented to their respective inputs. In this case, the unit delay 206 provides a unit delay for the output of the summer 206. After the output signal of the summer 204 is delayed by the unit delay 206, the signal passes simultaneously to the gain block 208, where the signal is multiplied by the coefficient represented by 1A1, and to the gain block 210, where the signal is multiplied by the coefficient represented by 1B1. After the signal which is presented to the gain block 210 is multiplied by the coefficient represented by 1B1, the signal is applied to one of the inputs of the summer 212. The summer 212 adds together the signal from the output of the summer 204 and the signal from the output of the gain block 210. The resulting sum of these signals is applied to the input of the gain block 214, where it is multiplied by the coefficient represented by 1C. The output signal of the gain block 214 is the output signal of stage A of this filter.

The values of coefficients 1A1, 1B1 and 1C as well as coefficients 2A1, 2A2, 2B1, 2B2, 2C, 3A1, 3A2, 3B1, 3B2 and 3C are shown in FIG. 5. The coefficients shown in FIG. 5 are chosen to produce an elliptic high pass filter which preferably includes a cutoff frequency of about 50 Hz, a passband gain of about 0 dB, a passband ripple of about 0.01 dB, a stopband corner frequency of about 30 Hz, and a stopband ripple of about 39 dB. The sample rate of this filter is preferably about 500 samples per second. It will be clear to those skilled in the art that the coefficient values of FIG. 5 are preferred values which may be modified to vary the cutoff frequency and other filter properties as desired.

It should also be noted that the gain of the high pass filter 22 at the stated cutoff frequency of about 50 Hz is preferably about −0.01 dB and not −3 dB as is sometimes specified. This is because the preferred passband ripple specification is 0.01 dB, and the cutoff frequency is considered to be the frequency below which the passband ripple specification is exceeded. The high pass filter 22 of the preferred embodiment also preferably has an attenuation of about 3 dB at 41.77 Hz.

The output signal of the gain block 208 is presented to the input of the summer 204, where it is added to the input ECG signal presented at the high pass filter 22 as input signal 202. Of course, the output signal from the gain block 208 and which is presented to the summer 204 has been delayed so that when it is added to the input signal 202 at the summer 204, the input signal 202 is a part of the ECG signal later in time than the part of the ECG signal which has been produced as the output signal of the gain block 208.

It is important to note that the output signal of the summer 204 contains a new part and an old part. The new part of the output signal of the summer 204 is the addition of the current ECG signal presented to the high pass filter 22 as input signal 202. The old part of the output signal of the summer 204 is the output signal of the gain block 208 which is added to the input ECG signal presented at the high pass filter 22 as input signal 202. But, after the input ECG signal has been added to the output signal of the gain block 208, the resulting output signal of the summer 204 is passed through the unit delay 206 and the gain block 208 back to be added to the input ECG signal at the summer 204. In this way, the ECG signal has a continuous existence as it is cycled through the loop from the summer 204 through the unit delay 206 and the gain block 208 back to the summer 204. It is because of the continuous existence of the influence of the ECG signal that this type of filter is called an "Infinite Impulse Response" (IIR) filter.

The output signal of the gain block 214 is the output signal of stage A. The output signal of the gain block 214 is presented to the input of stage B at the summer 216 where the output signal of stage A is added to the output signal of the gain block 224 and the output signal of the gain block 226, which will be described later. The output signal of the summer 216 is simultaneously presented to the unit delay 218 and the summer 230. The unit delay 218 delays the output signal from the summer 216 by a predetermined unit time period. The output of the unit delay 218 is sent simultaneously to three different places. The output signal of the unit delay 218 is presented to the gain block 224, where it is multiplied by the coefficient represented by 2A1. The output signal of the unit delay 218 is also presented to the gain block 222, where it is multiplied by the coefficient represented by 2B1. The output signal of the unit delay 218 is also presented to the unit delay 220, which delays the signal by a predetermined unit time period. The output signal of the gain block 222 is then presented to the summer 230. The signal from the output of the unit delay 220 is simultaneously presented to the gain block 228, where it is multiplied by the coefficient represented by 2B2, and to the gain block 226, where it is multiplied by the coefficient represented by 2A2. The output signal of the gain block 228 is presented to the summer 230. The summer 230 arithmetically adds together the signals received from the output of the summer 216, the output of the gain block 222, and the output of the gain block 228. The output of the summer 230 is then presented to the input of the gain block 232, where it is multiplied by the coefficient represented by 2C. The output signal of the gain block 232 is the output signal of stage B of the preferred form of the high pass filter 22.

The output signal of the gain block 232 is presented to the input of stage C at the summer 234 where the output signal of stage B is added to the output of the gain block 242 and the output of the gain block 244, as will be described in further detail below. The output signal of the summer 234 is simultaneously presented to the unit delay 236 and the summer 248. The unit delay 236 delays the output signal from the summer 234 by a predetermined unit time period. The output signal of the unit delay 236 is presented simultaneously to three different places. The output signal of the unit delay 236 is presented to the gain block 242, where it is multiplied by a coefficient represented by 3A1. The output signal of the unit delay 236 is also presented to the gain block 240, where it is multiplied by a coefficient represented by 3B1. The output signal of the unit delay 236 is also presented to the unit delay 238, which delays the signal by a predetermined unit time period. The output signal of the gain block 240 is presented to the summer 248. The signal at the output of the unit delay 238 is simultaneously presented to the gain block 246, where it is multiplied by a coefficient represented by 3B2, and to the gain block 244, where it is multiplied by a coefficient represented by 3A2. The output signal of the gain block 246 is presented to the summer 248. The summer 248 arithmetically adds together the output signals of the summer 234, the output signal of the gain block 240, and the output signal of the gain block 246. The output signal of the summer 248 is presented to the input of the gain block 250, where it is multiplied by a coefficient represented by 3C. The output signal of the gain block 250 is the output signal of stage C of the high pass filter 22 and the output signal 254 of the high pass filter 22.

The high pass filter 26 which is shown in FIG. 1 as being between the adaptive line noise canceler 20 and the wideband noise detector 28 is identical in construction to the high pass filter 22 which is between the prefilter delay element 18 and the line noise detector 24 as described above. The high pass filter 26 will not be described separately here because the above description of the high pass filter 22 applies equally to the high pass filter 26 as well.

The ECG signal of a signal acquisition or monitoring device may also become contaminated by a signal induced from the power lines or power sources in the vicinity of the electrocardiography apparatus. The power line signal contamination is usually in the form of a sine wave at the power line frequency and is often at the third harmonic of the power line frequency. The existence of second harmonic contamination is also possible, but less common. The purpose of the line noise detector 24 in the present embodiment is to measure the amplitude of the power line interference in the ECG signal.

Referring to FIG. 7, the ECG signal is applied to the input 320 of the line noise detector 24. The QRS complex of the ECG signal has been removed by the QRS gate, as described above, so as to avoid measuring the line frequency energy contained in the QRS complex. The line noise detector 24 is preferably a type of incoherent demodulator known to those skilled in the art as a quadrature detector. This type of detector is preferably used to detect signals when the frequency of the signal is known but the phase is not known.

The type of quadrature detector described here is also preferably frequency selective. This frequency selective property is desirable because the ECG signal contains energy over a wide range of frequencies, whereas it is desired to detect line noise energy only at the power line frequency.

The signal at the input 320 of the line noise detector 24 is presented simultaneously to the multipliers 322 and 324, where it is multiplied by quadrature sine waves at the power line frequency from the quadrature sine wave generator 326, which will be described later. In particular, the ECG signal is preferably multiplied by a cosine wave in the multiplier 322, and the ECG signal is also separately multiplied by a sine wave in the multiplier 324. The effect of this multiplication is to shift or translate any signal component at the power line frequency to a frequency at or near zero Hz at the outputs of the multipliers 322 and 324. The other frequency components of the ECG signal are also shifted by a similar amount but appear at frequencies other than zero Hz at the multiplier outputs.

The signal outputs of the multipliers 322 and 324 are then preferably applied to the inputs of identical low pass filters 328 and 330, respectively. These low pass filters preferably have a cutoff frequency of about 0.2 Hz. Because of the frequency translation process, components of the ECG signal at frequencies between 59.8 Hz and 60.2 Hz (in the case of a 60 Hz power line frequency) will appear at the signal outputs of the multipliers 322 and 324 as signals at frequencies of 0 Hz to 0.2 Hz and, therefore, will preferably pass through the low pass filters 328 and 330. The other signal components of the ECG signal will be translated to higher frequencies which will not be allowed to pass through the low pass filters 328 and 330.

Because the translated line noise signals at the signal outputs of the low pass filters 328 and 330 are equal in amplitude and in a quadrature phase relationship, their magnitude can be found by squaring each of these signals and adding the resulting squared values. The output signals of the low pass filters 328 and 330 are presented to the squarers 332 and 334 respectively. The output signals of the squarers are then applied to the summer 336. The numerical value at the output of the summer 336 is theoretically the square of one half the magnitude of the signal component at the power line frequency. The output signal of the summer 336 is also the output signal 338 of the line noise detector 24.

Figures 8A, 8B:
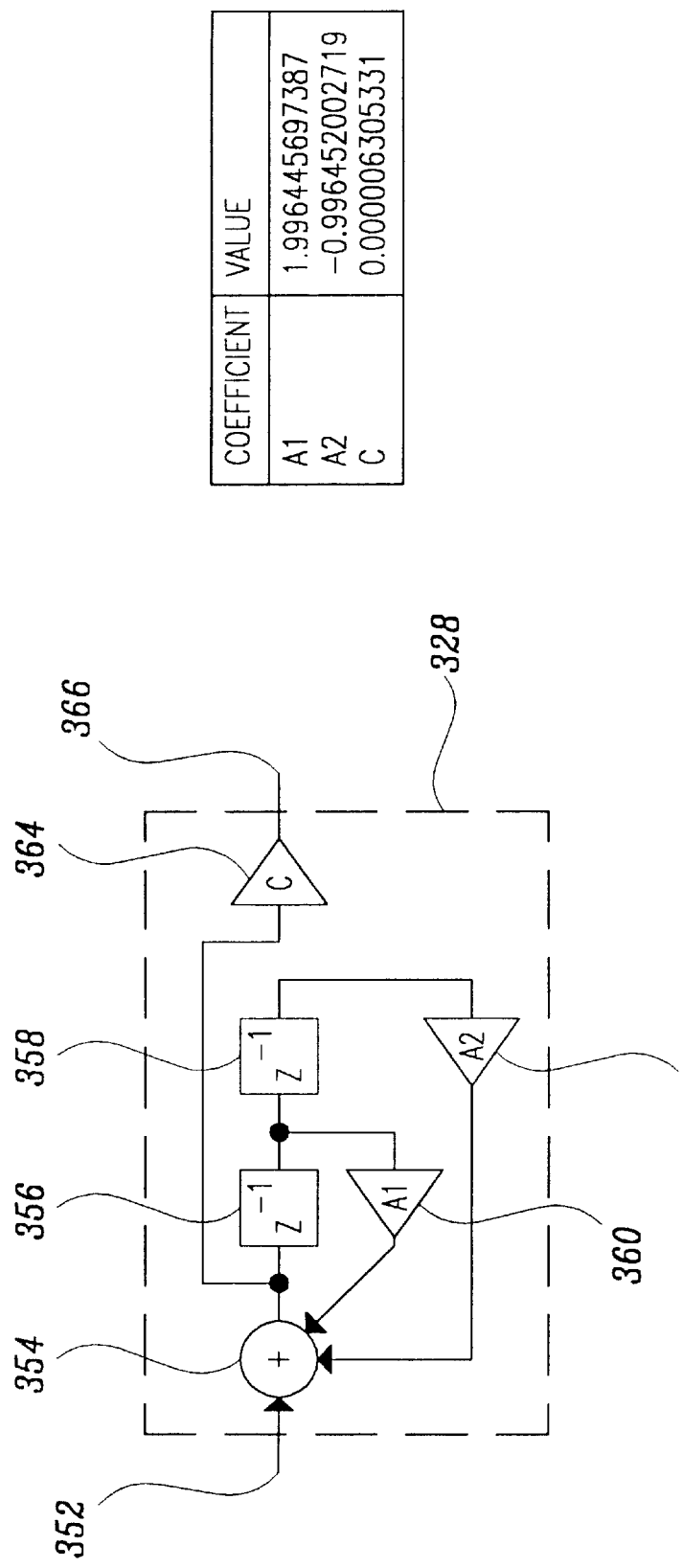
FIG. 8A is a detailed block diagram of the preferred form of the low pass filter of the present invention as shown from the block diagram of the line noise detector as shown in FIG. 7.
FIG. 8B is a table of coefficients used in the preferred form of the realization of the low pass filter of FIG. 8A.

The low pass filter 328, shown in FIGS. 7 and 8A, is preferably a second order Butterworth low pass filter having a cutoff frequency of about 0.2 Hz. These Butterworth filters may be realized in many different ways. One class of realizations is active realizations utilizing operational amplifiers, resistors and capacitors. Another class of realizations is passive realizations utilizing inductors, resistors and capacitors. Another class of realizations is discrete time digital realizations utilizing summers, unit delays and gain blocks. Digital realizations can be built with dedicated electronic hardware or, alternatively, can be implemented by means of a program running on a digital computer.

The preferred embodiment described here is a preferably recursive digital realization. As shown in FIG. 8A, the signal at the input 352 of the low pass filter 328 is preferably immediately passed to the summer 354. At the summer 354, the input signal at the low pass filter input 352 is added to the output signal of the gain block 360 and the output signal of the gain block 362, which will be described later. The signal at the output of the summer 354 is simultaneously presented to the unit delay 356 and the gain block 364. The unit delay 356 preferably delays the output signal from the summer 354 by a predetermined unit time period. The output signal of the unit delay 356 is presented simultaneously to the input of the unit delay 358 and the input of the gain block 360. The gain block 360 multiplies the signal at the output of the unit delay 356 by a coefficient represented by A1 as shown in FIG. 8B. The unit delay 358 preferably delays the output signal from the unit delay 356 by a predetermined unit time period. The signal at the output of the unit delay 358 is then presented to the input of the gain block 362, where it is multiplied by a coefficient represented by A2 as shown in FIG. 8B. At the gain block 364, the signal from the output of the summer 354 is multiplied by a coefficient represented by C as shown in FIG. 8B. The output signal of the gain block 364 is immediately presented to the squarer 332 of the line noise detector 24 as the output signal 366.

The preferred values of coefficients A1, B1 and C are shown in FIG. 8B. These preferred coefficient values are valid at a sample rate of about 500 samples per second. It will be clear to those skilled in the art that the coefficient values referred to above may be modified to vary the cutoff frequency and other filter properties as desired.

The low pass filter 330 is identical in construction to the low pass filter 328 and will not be described separately here because the above description of the low pass filter 328 applies equally to the low pass filter 330 as well as is shown in FIGS. 8A and 8B.

Figures 9A, 9B:
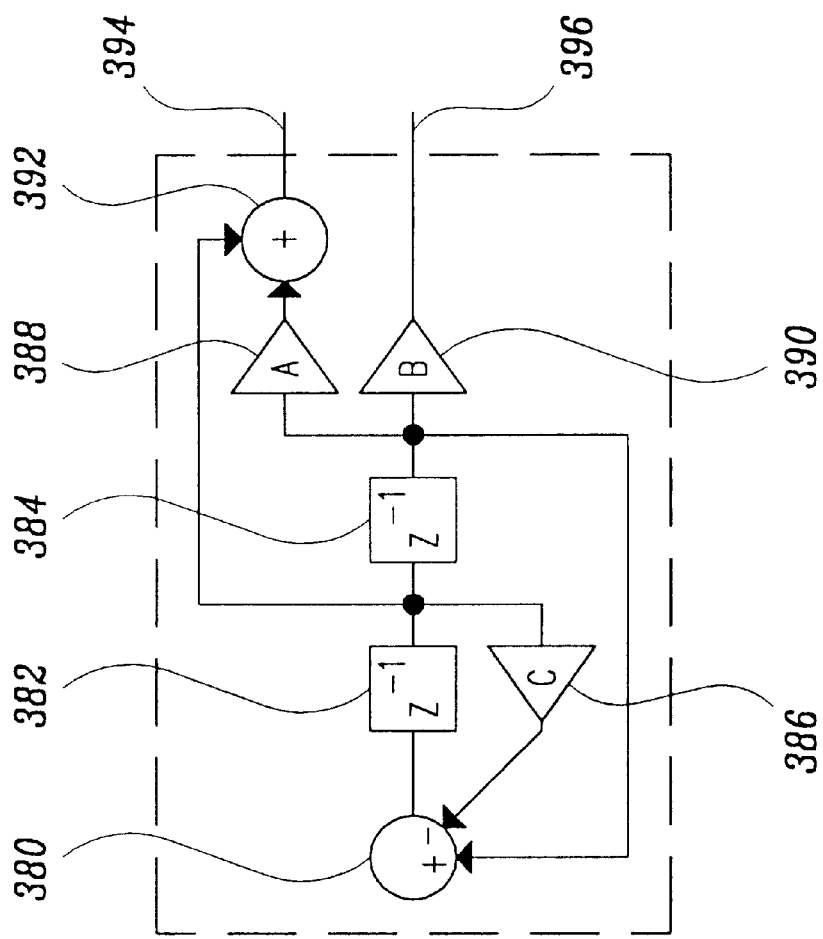
FIG. 9A is a detailed block diagram of the preferred form of the quadrature sine wave oscillator of the line noise detector as shown in the block diagram of FIG. 7.
FIG. 9B is a table of coefficients used in the realization of the quadrature sine wave oscillator of FIG. 9A.

The quadrature sine wave generator 326 as shown in FIG. 7 is preferably a discreet time digital oscillator which has two outputs which produce sine waves in a quadrature (90 degree) phase relationship. FIG. 9A shows a block diagram of the preferred form of the quadrature sine wave generator 326. The cosine output 394 presents a sinusoidal wave that leads the sine output 396 by 90 degrees. In the preferred form of the present embodiment, the frequency of the quadrature sine wave generator 326 must be close to the frequency of the power line; therefore, where the power line frequency is about 60 Hz, the internal oscillator frequency must be about 60 Hz; and, where the power line frequency is about 50 Hz, the internal oscillator frequency must be about 50 Hz.

At the summer 380, the input signal at the output of the unit delay 384 is subtracted from the output of the gain block 386 as described below. The signal at the output of the summer 380 is then presented to the unit delay 382. The unit delay 382 preferably delays the output signal from the summer 380 by a predetermined unit time period. The output signal of the unit delay 382 is then presented simultaneously to the input of the unit delay 384, the input of the gain block 386 and the input of the summer 392. The unit delay 384 preferably delays the output signal from the unit delay 382 by a predetermined unit time period. The output of the unit delay 384 is then presented simultaneously to the input of the gain block 388, the input of the gain block 390 and the negative input of the summer 380. The gain block 386 multiplies the signal at the output of the unit delay 382 by a coefficient represented by C as shown in FIG. 9B. The gain block 388 multiplies the signal at the output of the unit delay 384 by a coefficient represented by A as shown in FIG. 9B. The gain block 390 preferably multiplies the signal at the output of the unit delay 384 by a coefficient represented by B as shown in FIG. 9B. The output of the gain block 390 is also the sine output 396 of the quadrature sine wave generator 326. The summer 392 adds the output of the unit delay 382 to the output of the gain block 388. The output of the summer 392 is also the cosine output 394 of the quadrature sine wave generator 326.

The quadrature sine wave generator 326 of the present embodiment is similar to a second order IIR digital filter but has no signal input. The quadrature sine wave generator 326 preferably has poles on the unit circle of the Z plane, so it oscillates indefinitely without decaying or growing in amplitude. Before the sine wave generator can operate, the unit delays must be initialized with the proper values. One way to do this is to set the numerical value in the unit delay 382 to the desired peak amplitude of the sinusoidal outputs and set the numerical value in the unit delay 384 to zero. The frequency of oscillation is determined by the sampling rate and the value of a coefficient represented by C as shown in FIG. 9B.

The coefficients A, B and C each depend upon the desired frequency of oscillation which, as stated above, must be approximately equal to the power line frequency. The preferred values of the coefficients A, B and C of the quadrature sine wave generator 326 can be computed by the following formulas:

$A = -\cos(\omega T)$ $B = \sin(\omega T)$ $C = 2\cos(\omega T)$

Where $T = 1/F_s$ $\omega = 2\pi f_{osc}$ $F_s$ is the sample rate in samples per second.

$f_{osc}$ is the desired oscillator frequency in Hertz.

The values of the coefficients A, B and C for the preferred embodiment of the quadrature sine wave generator 326 are shown in FIG. 9B. The values shown are valid for a preferred sample rate of about 500 samples per second and an oscillator frequency of 60 Hz. The values of A, B and C may be calculated from the above formulas in the event that a different frequency of oscillation or sample rate is desired.

Figure 10:
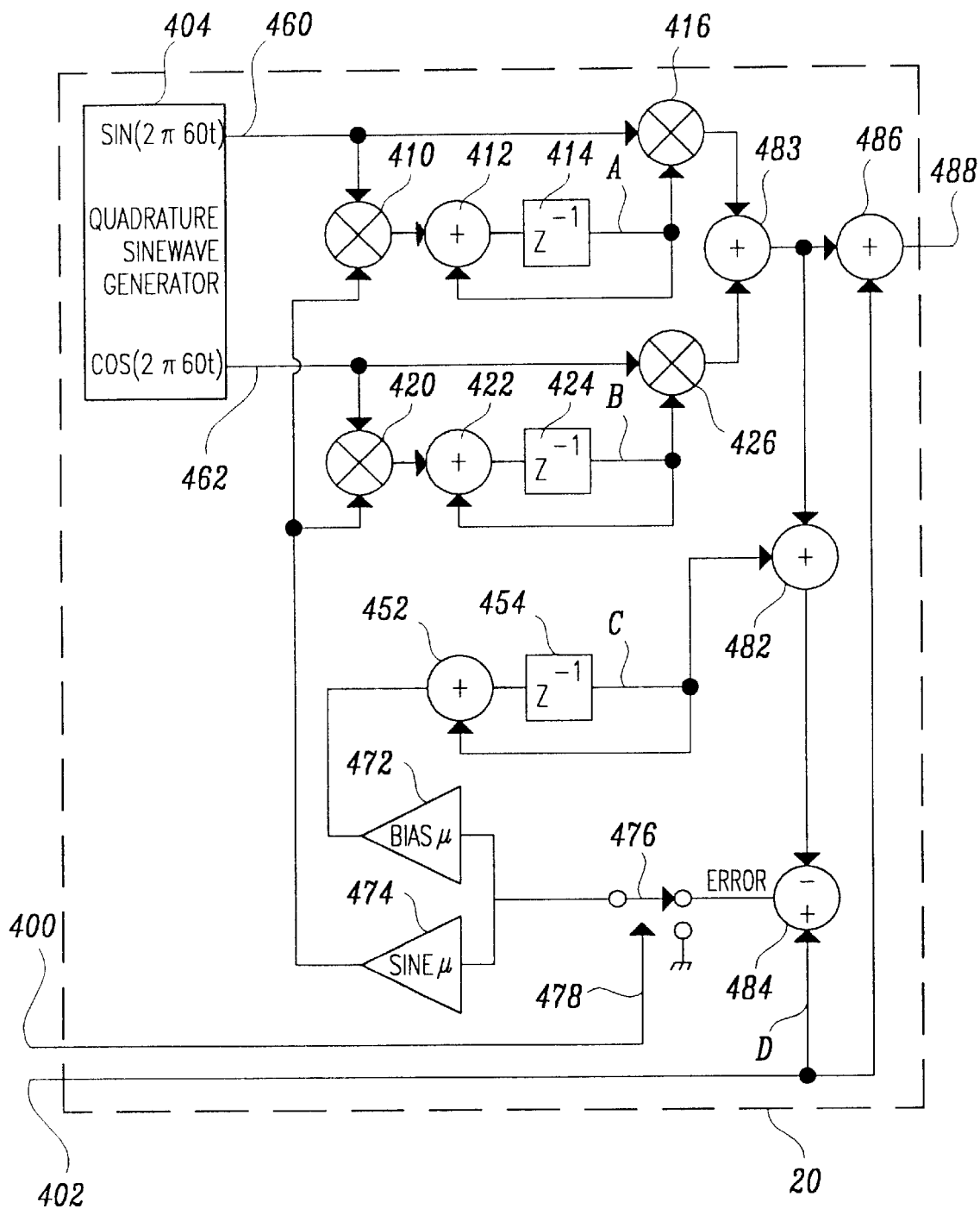
FIG. 10 is a block diagram of the preferred form of the adaptive line noise canceler of the present invention as shown from the block diagram of FIG. 1.

The adaptive line noise canceler 20 removes or reduces the amplitude of additive noise induced by nearby power-carrying conductors. The power line frequency is typically 60 Hz in the United States, while 50 Hz is common in Europe. As shown in FIG. 10, the adaptive line noise canceler 20 preferably contains an internal oscillator at the power line frequency. The well known LMS algorithm is preferably used to match the amplitude and phase of the oscillator signal to that of the line frequency component of the ECG signal. The oscillator signal is then subtracted from the ECG signal, thereby canceling the power line interference. In order to be effective, the frequency of the quadrature sine wave generator must be close to the frequency of the power line. Therefore, where the power line frequency is 60 Hz, the internal oscillator frequency must also be about 60 Hz, and where the power line frequency is 50 Hz, the internal oscillator frequency must be about 50 Hz.

A block diagram of the preferred form of the adaptive line noise canceler is shown in FIG. 10. The quadrature sine waves are generated by a quadrature sine wave generator 404. The quadrature sine wave generator 404 is similar to the quadrature sine wave generator 326, shown in FIGS. 7 and 9A, as an element of the line noise detector 24.

The sine wave at the output 460 of the quadrature sine wave generator 404 is presented to an input of the multiplier 416, where it is multiplied by a coefficient represented by A. This is the numeric value at the output of the unit delay 414. For convenience, the output of the unit delay 414 is also referred to herein and shown in FIG. 10 as coefficient A, and the output of the unit delay 424 is also referred to herein and shown in FIG. 10 as coefficient B. The cosine wave at the output 462 of the quadrature sine wave generator 404 is presented to an input of the multiplier 426, where it is multiplied by a coefficient represented by B. This is the numeric value at the output of the unit delay 424. The outputs of the multiplier 416 and the multiplier 426 are then summed together in the summer 480.

The process of multiplying the sine and cosine outputs of the quadrature sine wave generator 404 by coefficients represented by A and B and then summing these products can be represented by the following mathematical formula.

$$M \sin(\omega t + \theta) = A \sin(\omega t) + B \cos(\omega t)$$

Where

M is the peak amplitude of a sine wave.

$\omega$ is the frequency in radians per second of a sine wave.

t is time in seconds.

$\theta$ is the phase in radians of a sine wave.

The coefficients A and B are chosen so as to obtain a sine wave of the desired amplitude, M, and phase, $\theta$. The values of coefficients A and B may be computed by means of the following formulas:

$A = M \cos \theta$ $B = M \sin \theta$

As a result of the above discussion and formulas, the coefficients A and B may be chosen so as to produce a sinusoidal waveform of any desired amplitude and phase at the output of the summer 480.

The ECG signal is applied as the input signal 400 of the adaptive line noise canceler 20 via the summer 484 and simultaneously to the positive input of the summer 486. The sinusoidal wave at the output of the summer 480 is then applied to the negative input of the summer 486, where it is subtracted from the ECG signal.

In the preferred form of the present invention, coefficients A and B are preferably chosen to produce, at the output of the summer 480, a sinusoidal wave that matches the component of the ECG signal that is induced by the local power line. This sinusoidal wave is then subtracted from the ECG signal in the summer 486. The effect of this subtraction is to cancel the component of the ECG signal which was induced by the local power line. A clean ECG signal, from which the power line interference has been removed, is then produced at the output of the summer 486 and is simultaneously presented as the output signal 488 of the adaptive line noise canceler 20.

In the preferred form of the present invention, the coefficients are not computed by the formulas presented above, because the phase and amplitude of the potential power line interference are not known ahead of time to the noise detection system. Therefore, the coefficients are gradually adjusted by means of a simple adaptive process called the least mean square (LMS) algorithm.

The following description explains how coefficients A and B are adjusted to produce a sinusoidal wave whose amplitude and phase match the sinusoidal interference in the ECG signal. It should be noted the adaptive line noise canceler is a discrete time sampled data system; and, therefore, the steps presented below are performed at the system sample rate. Accordingly, the sample rate is preferably at least two times the highest frequency component in the signals being processed. Although the sample rate in the preferred embodiment is about 500 samples per second, it may be modified according to the particular system requirements.

Referring again to FIG. 10, the sinusoidal signal at the output of the summer 480 is applied to the summer 482, where it is added to the output signal of the unit delay 454. The output signal of the unit delay 454 is a value that is intended to cancel the DC component of the ECG signal. The value at the output of the unit delay 454 is also referred to as coefficient C and is discussed in more detail below.

The value at the output of the summer 482 is applied to the negative input of the summer 484, where it is subtracted from the ECG signal at the input 400. The output signal of the summer 484 is called the error signal. This error signal passes through the switch 476 and is presented simultaneously to the gain block 472 and the gain block 474.

The gain block 474 multiplies the error signal by a constant called "sine $\mu$." In the preferred embodiment, sine $\mu$ has the preferred value of about 0.0435, but larger or smaller values could be used at the discretion of the designer. The value of sine $\mu$ is selected for the best tradeoff between the speed and stability of adaptation. The use of larger values of sine $\mu$ will cause the coefficients to be adjusted faster but with less accuracy. The use of smaller values of sine $\mu$ will cause the coefficients to be adjusted more slowly but with more accuracy.

The output signal of the gain block 474 is presented simultaneously to the multiplier 410 and the multiplier 420.

The multiplier 410 multiplies the sine wave at the output signal 460 of the quadrature sine wave generator 404 by the output signal of the gain block 474. The resulting value at the output of the multiplier 410 is used as a small "adjustment" to be added to the value of the coefficient represented by A in the unit delay 414. The output signal of the multiplier 410 is presented to the summer 412, where it is added to the current value in the unit delay 414. The unit delay 414 delays the signal from the output of the summer 412 by one predetermined unit time period. After one unit time period, the value represented by coefficient A in the unit delay 414 is replaced with the "adjusted value" from the output of the summer 412.

The multiplier 420 multiplies the cosine wave at the output 462 of the quadrature sine wave generator 404 by the output of the gain block 474. The resulting value at the output of the multiplier 420 is used as a small "adjustment" to be added to the value represented by coefficient B in the unit delay 424. The output of the multiplier 420 is then presented to the summer 422 where it is added to the current value in the unit delay 424. The unit delay 424 delays the signal from the output of the summer 422 by one predetermined unit time period. After one unit time period, the value represented by coefficient B in the unit delay 424 is replaced with the "adjusted value" from the output of the summer 422.

The value represented by coefficient C is called the "bias weight." Coefficient C is preferably stored in the unit delay 454 and is presented simultaneously to the summer 452 and the summer 482. Because the output of the summer 482 is connected to the negative input of the summer 484, the value represented by coefficient C is, in effect, subtracted from the error signal at the output of the summer 484. Therefore, the value represented by coefficient C is an estimate of the DC component of the ECG signal at the input 400, and removing this DC component improves the accuracy of the coefficient adaptation process.

The error signal at the output of the summer 484 passes through the switch 476 and is presented to the gain block 472, where it is multiplied by a constant value called "bias $\mu$." In the preferred embodiment, bias $\mu$ has the value of about 0.04. The preferred value of bias $\mu$ is selected for the best tradeoff between speed and stability of the adaptation of the value represented by coefficient C.

The resulting value at the output of the gain block 472 is used as a small "adjustment" to be added to the value represented by coefficient C in the unit delay 454. The output of the gain block 472 is presented to the summer 452 where it is added to the current value in the unit delay 454. The unit delay 454 delays the signal from the output of the summer 452 by one predetermined unit time period. After the one unit time period, the value represented by coefficient C in the unit delay 454 is replaced with the "adjusted value" from the output of the summer 452.

Figure 14A:
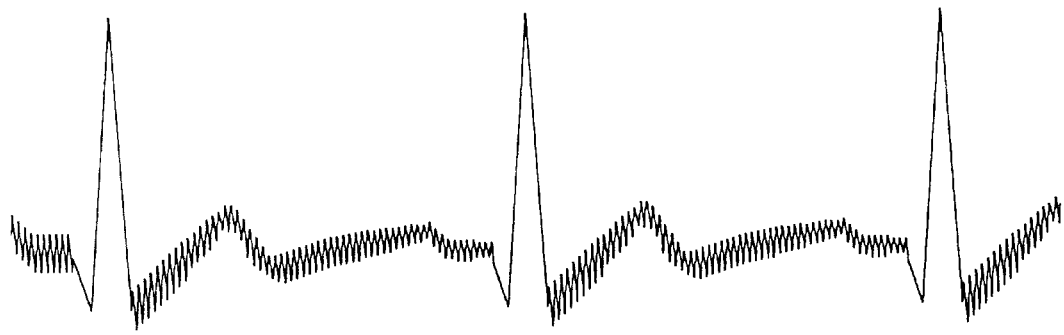
FIG. 14A is a graph of an ECG waveform with an excessive amount of power line interference.
Figure 14B:
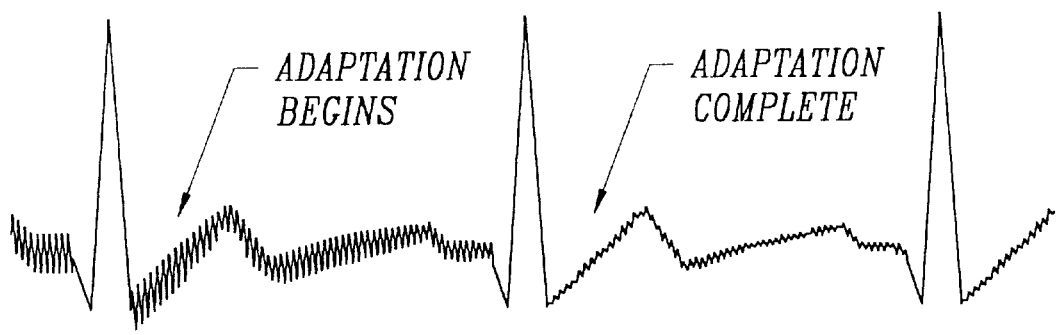
FIG. 14B is a graph of the adaptive line noise canceler output as the adaptive process to remove line noise converges.

FIG. 14A is a graph illustrating an ECG waveform with an excessive amount of 60 Hz interference. FIG. 14B shows the effect of the operation of the noise canceler of the present invention. From the moment the noise canceler is turned on, the coefficients are adjusted by means of the LMS algorithm. As the values of the coefficients approach their optimum values, the cancellation of the 60 Hz noise steadily improves until adaptation is complete. Note the absence of interference and the clarity of detail after the adaptive process has converged.

The main component of power line interference is a sinusoidal wave at the fundamental frequency of the power line. Due to the symmetric distortion of the power line waveform, a strong third harmonic component can also exist. Second harmonic interference is less common. In the United States, for example, the fundamental frequency is about 60 Hz, and the third harmonic would be about 180 Hz. In Germany, the fundamental frequency is about 50 Hz, and the third harmonic is about 150 Hz.

One problem with applying the LMS algorithm to the cancellation of noise in the ECG signal arises from the perturbation of the coefficients by the QRS complex. The QRS complex typically has a significant amount of energy at the power line frequency. In addition, the QRS complex usually has a high amplitude. Because of this, the coefficients tend to become misadjusted slightly during the QRS phase of the ECG signal, with the result that a small amount of ringing is visible in the ECG waveform after the end of the QRS complex.

A solution for this problem is to inhibit the update of the coefficients during the QRS complex. In the present invention, the QRS gate signal is used to control the updating of coefficients during the QRS complex. The QRS gate is preferably a Boolean signal that is high (true) during the QRS complex and low (false) at all other times. In the preferred form of the present invention, the slope of the ECG signal may be used to create the QRS gate. This is possible because the slope of the ECG signal is very high during the QRS complex and very low during other parts of the ECG signal. Therefore, the slope can be used to identify the QRS complex. A conventional slope determination and signal processing system may be used to generate the QRS gate signal. An example of this type of system is disclosed in U.S. Pat. No. 5,259,387 which provides a method which can be used to generate the QRS gate pulse. The absolute value of the slope is preferably measured so that the rise as well as the fall in the ECG signal may be detected. This absolute slope is filtered and then compared with a long-term maximum slope. The ratio of the absolute slope and long-term maximum slope is used to control the bandwidth of a muscle artifact filter in such a manner that the bandwidth of the filter is greater during the QRS complex than during the remainder of the ECG signal. In the preferred form of the present invention, the QRS gate signal is generated by means of logic which causes the QRS gate to be true when the filter bandwidth is equal to or greater than about 77 Hz and false when the filter bandwidth is less than about 77 Hz. This provides a simple and economical way of generating the QRS gate signal when the muscle artifact filter of the above-referenced patent is employed in an ECG signal processing signal. A switch 21 as shown in FIG. 1 of the present invention, may connect the filtered and delayed ECG signal, either before or after adaptive line noise canceller 20, to a muscle artifact filter such as in above referenced U.S. Pat. No. 5,259,387.

Referring now to FIG. 10, the QRS gate signal is presented to the adaptive line noise canceler 20 via the QRS gate input 402 to the control input of the switch 476. Therefore, during the QRS complex of the ECG signal, the QRS gate signal at the control input of the switch 476 is high. The switch 476 connects the inputs of the gain blocks 472 and 474 to ground or zero volts. In this state, the output of the gain block 414 is zero, which causes a zero value to be presented to the multipliers 410 and 420. As a result, a zero value is presented to the summers 412 and 422. Also, since the output of the gain block 472 is zero, a zero value is presented to the summer 452. This causes the values of the coefficients in the unit delays 414, 424 and 454 to remain constant.

When the control input of the switch 476 is low, the switch 476 connects the error signal at the output of the summer 484 to the gain blocks 472 and 474. In this state, coefficient updating is enabled.

Figure 11A:
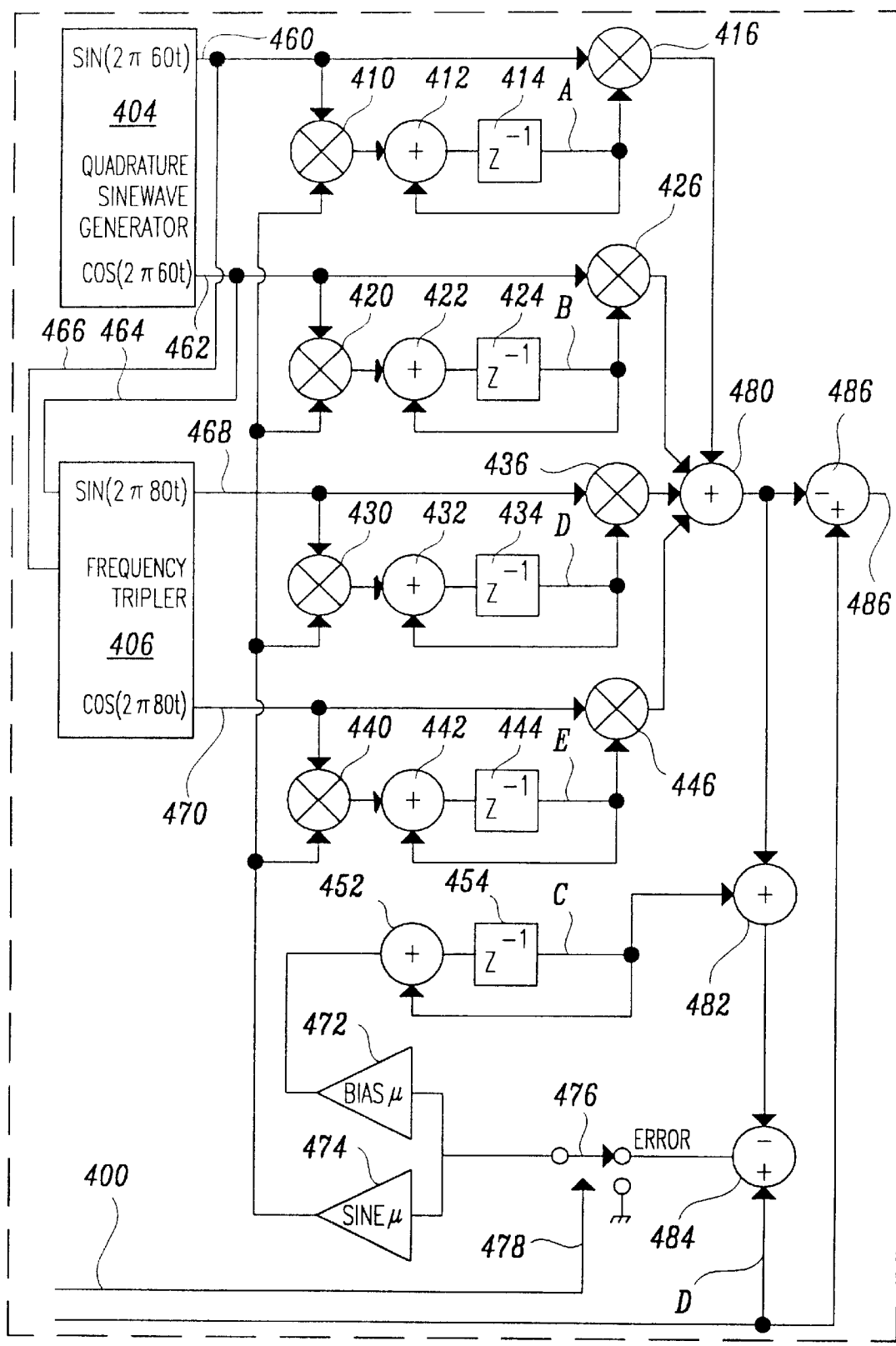
FIG. 11A is a block diagram of an improved adaptive line noise canceler of the present invention as shown from the block diagram of FIG. 1 with improvements permitting the cancellation of third harmonic power line interference.

Although the adaptive line noise canceler 20 of FIG. 10 is effective at reducing the amplitude of the fundamental power line frequency, this embodiment does nothing to eliminate third harmonic interference. FIG. 11A shows an alternate version of the adaptive power line noise canceler of the present invention. The adaptive power line noise canceler of FIG. 11A is identical to the adaptive power line noise canceler of FIG. 10 except that components have been added that enable the alternate embodiment to cancel the third harmonic interference in addition to the fundamental frequency interference.

In order to cancel the third harmonic frequency component, a source of quadrature sinusoids at about three times the power line frequency is needed. A separate oscillator, similar to the quadrature sine wave generator 404, may be employed. However, in the embodiment shown in FIG. 11A, a frequency tripler is used to produce the quadrature sinusoids at a frequency of three times the fundamental power line frequency. Referring to FIG. 11A, the signal at the sine wave output 460 of the quadrature sine wave generator 404 is presented to the input 466 of the frequency tripler 406. Also, the signal at the cosine wave output 462 of the quadrature sine wave generator 404 is presented to the input 464 of the frequency tripler 406. The quadrature sinusoids are produced at three times the input frequency at the sine output 468 and the cosine output 470 of the frequency tripler 406. The principle of operation of the frequency tripler 406 is described in detail below.

In addition to the frequency tripler 406, the added elements of the adaptive line noise canceler of FIG. 11A include the multipliers 430, 440, 436 and 446, the summers 432 and 442, and the unit delays 434 and 444. These added elements enable the line noise canceler of FIG. 11A to cancel third harmonic power line noise in the same manner as the fundamental power line frequency.

The output of the gain block 474 is presented simultaneously to the multipliers 410, 420, 430 and 440. The multiplier 430 multiplies the third harmonic sine wave at the output 468 of the frequency tripler 406 by the output of the gain block 474. The resulting value at the output of the multiplier 430 is used as a small "adjustment" to be added to the value represented by coefficient D in the unit delay 434. The output of the multiplier 430 is then presented to the summer 432 where it is added to the current value in the unit delay 434. The unit delay 434 delays the signal from the output of the summer 432 by one predetermined unit time period. After one unit time period, the value represented by coefficient D in the unit delay 434 is replaced with the "adjusted value" from the output of the summer 432.

The multiplier 440 multiplies the cosine wave at the output 470 of the frequency tripler 406 by the output of the gain block 474. The resulting value at the output of the multiplier 440 is used as a small "adjustment" to be added to the value represented by coefficient E in the unit delay 444. The output of the multiplier 440 is then presented to the summer 442 where it is added to the current value in the unit delay 444. The unit delay 444 delays the signal from the output of the summer 442 by one predetermined unit time period. After one predetermined unit time period, the value represented by coefficient E in the unit delay 444 is replaced with the "adjusted value" from the output of the summer 442.

Figure 11B:
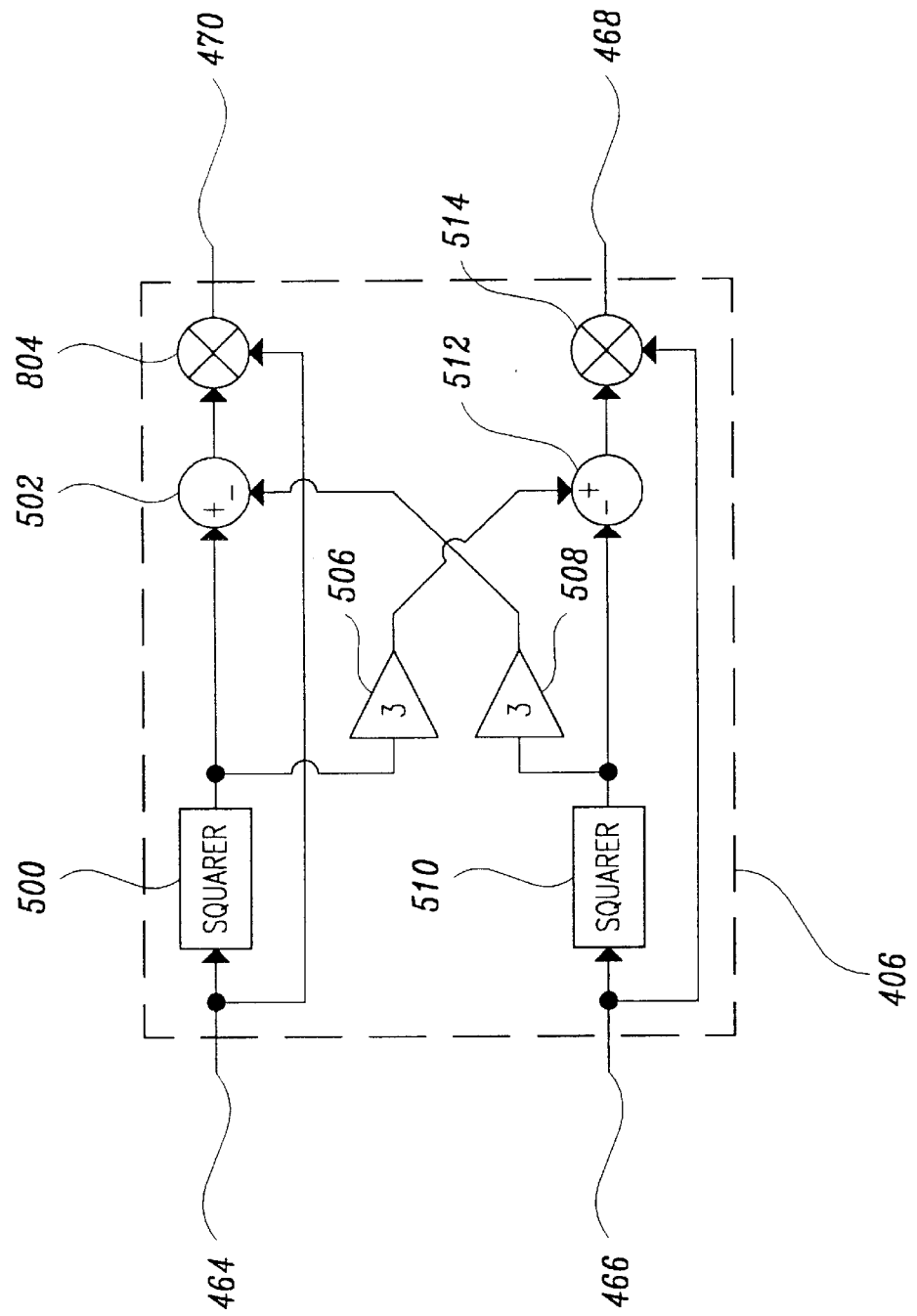
FIG. 11B is a block diagram of the frequency tripler of the improved adaptive line noise canceler of FIG. 11A.

FIG. 11B is a block diagram illustrating the preferred form of the frequency tripler 406 of FIG. 11A. The quadrature sine waves are presented to the frequency tripler 406 at the cosine input 464 and the sine input 466. The frequency tripler 406 produces quadrature sine waves at three times the input frequency at the cosine output 470 and the sine output 468.

The quadrature sinusoids at the input of the frequency tripler can be regarded as a rotating unit vector at the fundamental frequency. This is expressed mathematically as $e^{j\omega t}$.

It is desired to obtain a rotating vector at three times the input frequency:

$$e^{j3\omega t}=(e^{j\omega t})^3 \qquad \text{eq. 1}$$

According to Euler's identity:

$$e^{j\omega t}=\cos(\omega t)+j\sin(\omega t) \qquad \text{eq. 2}$$

$$e^{j3\omega t}=\cos(3\omega t)+j\sin(3\omega t) \qquad \text{eq. 3}$$

Substituting eq. 2 and eq. 3 into eq. 1, the following formula is obtained:

$$\cos(3\omega t)+j\sin(3\omega t)=(\cos(3\omega t)+j\sin(3\omega t))^3 \qquad \text{eq. 4}$$

Performing the indicated operations and collecting real and imaginary terms, the following formulas are obtained:

$$\cos(3\omega t)=\cos(\omega t)(\cos^2(\omega t)-3\sin^2(\omega t)) \qquad \text{eq. 5}$$

$$\sin(3\omega t)=\sin(\omega t)(3\cos^2(\omega t)-\sin^2(\omega t)) \qquad \text{eq. 6}$$

Referring to FIG. 11B, it can be seen that the third harmonic signal at the cosine output 470 of the frequency tripler 406 is formed in accordance with equation 5. The quadrature sinusoids at the fundamental power line frequency are presented to the frequency tripler 406 at the cosine input 464 and the sine input 466. In equations 5 and 6, the signal at the cosine input 464 is represented as $\cos(\omega t)$, and the signal at the sine input 466 is represented as $\sin(\omega t)$.

As shown in FIG. 11B, the signal at the cosine input 464 is presented simultaneously to the squarer 500 and the multiplier 504. The squarer 500 forms the square of the signal at the cosine input 464. Because the signal at the input of the squarer 500 is represented mathematically as $\cos(\omega t)$, the signal at the output of the squarer 500 is $\cos^2(\omega t)$.

The signal at the sine input 466 is presented simultaneously to the squarer 510 and the multiplier 514. The squarer 510 forms the square of the signal at the sine input 466. Because the signal at the input of the squarer 510 is represented mathematically as $\sin(\omega t)$, the signal at the output of the squarer 510 is $\sin^2(\omega t)$.

The output of the squarer 500 is then presented to the positive input of the summer 502. The signal at the output of the squarer 510 is presented to the gain block 508, where the value of the output of the squarer 510 is multiplied by 3. The output of the gain block 508 is presented to the negative input of the summer 502, where the output of the gain block 508 is subtracted from the signal at the output of the squarer 500. The output of the summer 502 is presented to the input of the multiplier 504, where the output of the summer 502 is multiplied by the signal at the cosine input 464. The signal at the output of the multiplier 504 is presented to the cosine output 470. The signal at the cosine output 470 is represented in equation 5 as $\cos(3\omega t)$.

The signal at the output of the squarer 500 is presented to the gain block 506 where the value of the output of the squarer 500 is multiplied by 3. The output of the gain block 506 is presented to the positive input of the summer 512. The output of the squarer 510 is presented to the negative input of the summer 512, where it is subtracted from the signal at the output of the gain block 506. The signal at the output of the summer 512 is presented to the input of the multiplier 514 where it is multiplied by the signal at the sine input 466. The signal at the output of the multiplier 514 is then presented to the sine output 468. The signal at the sine output 468 is represented in equation 6 as $\sin(3\omega t)$.

Figure 12A:
FIG. 12A is a graphic representation of a normal ECG signal with acceptably low levels of 50 Hz, 60 Hz and wideband noise.
Figure 12B:
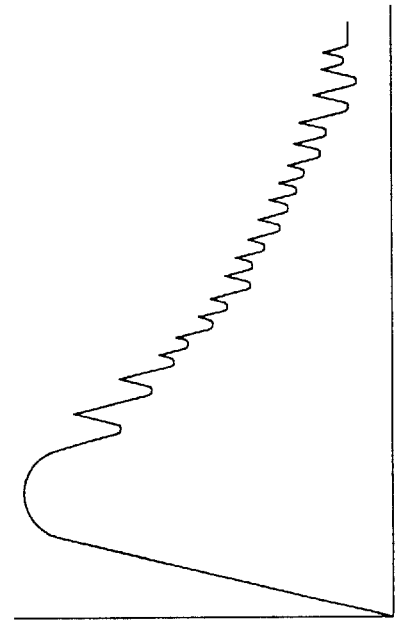
FIG. 12B is a graphic representation of the magnitude spectrum of the ECG of FIG. 12A.

FIG. 12A is a time domain plot of a normal ECG signal with acceptably low levels of 50 Hz, 60 Hz and wideband noise. FIG. 12B is a graphic representation of a Fourier magnitude spectrum of the ECG signal of FIG. 12A, showing magnitude versus frequency.

Figure 13A:
FIG. 13A is a graphic representation of an ECG signal with an added level of 60 Hz noise.
Figure 13B:
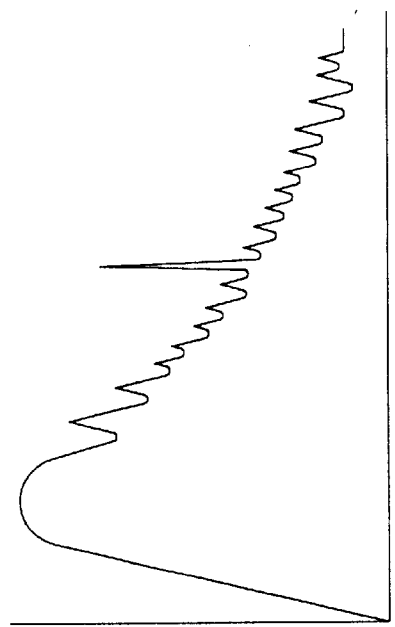
FIG. 13B is a graphic representation of the magnitude spectrum of the ECG of FIG. 13A.

FIG. 13A is a time domain plot of an ECG signal similar to the signal of FIG. 12A but with an added 60 Hz line noise signal whose amplitude is about 30 microvolts peak. The 30 82 v peak value is chosen for this example because it is considered to be a marginally acceptable level of line frequency noise for ECG analysis purposes. The magnitude spectrum of the resulting signal, as shown in FIG. 13B, demonstrates that the resulting power spectral density in the vicinity of 60 Hz is significantly greater than the surrounding power spectral density when analyzed with a narrow bandwidth. Therefore, the resulting power spectral density at 60 Hz of the clean signal shown in FIG. 12B and the noisy ECG signal of FIG. 13B is significantly greater than the surrounding power spectral density when analyzed with a narrow bandwidth. Therefore, detecting the presence of power line interference may be accomplished by comparing the power spectral density at the power line frequency with that of surrounding frequencies.

As shown in FIG. 1, before the ECG signal reaches the input of the wideband noise detector 28, the ECG signal passes through the baseline wander filter 16, the prefilter delay element 18, the adaptive line noise canceler 20, the switch 36 and the high pass filter 26. The purpose of the wideband noise detector is to detect muscle artifact and other forms of wideband noise contamination in the ECG signal. This is difficult because the ECG signal and muscle artifact usually occupy the same frequency range. Most of the wideband energy of the ECG signal is contained in the QRS complex; therefore, the problem is solved by blanking the QRS complex in the same manner as described above regarding the line noise detector. The portion of the ECG signal that remains after the QRS complex is removed contains only low frequency information, which is then filtered and removed by the high pass filter 26. The muscle artifact and other wideband noises contain higher frequency information, which is passed by the high pass filter 26 and then measured by the wideband noise detector 28. The signal reaching the input of the wideband noise detector 28 is a high pass filtered ECG signal with the QRS complex removed. The output of wideband noise detector 28 consists of an estimate of the amount of high frequency energy (above approximately 42 Hz) which is present in the ECG signal.

As stated previously, the function of the wideband noise detector 28 is to measure the amplitude of higher frequency noise from sources such as muscle artifact and electrode movement. The wideband noise detector 28 is sensitive to noise signals over a wide range of frequencies. However, it is not desired to measure the baseline wander or low frequency components of the ECG signal such as the P wave or T wave. In order to prevent the wideband noise detector 28 from measuring these signal components, the signal passes through the high pass filter 26 before being presented to the input of the wideband noise detector 28. Similarly, it is not desirable for the wideband noise detector 28 to be sensitive to power line frequency noise. Therefore, the ECG signal passes through the adaptive line noise canceler 20 before being presented to the input of the wideband noise detector 28. Another problem is that the QRS complex of the ECG signal contains a significant amount of energy in the frequency range passed by the high pass filter 26. To solve this problem, the QRS complex of the ECG signal is blanked out by the switch 36 and the switch 38 before being presented to the input of the wideband noise detector 28. The signal at the input of the wideband noise detector 28 contains only the frequency components which are above approximately 40 Hz and contains no QRS complex, line frequency noise or baseline wander. Although these components eliminate some of the noise that it is desired to measure, because muscle artifact contains frequency components below 40 Hz, muscle artifact and electrode movement noise also contain significant energy above 40 Hz. In the preferred form of the present invention, it is the energy above 40 Hz that is measured by the wideband noise detector 28.

Figure 15:
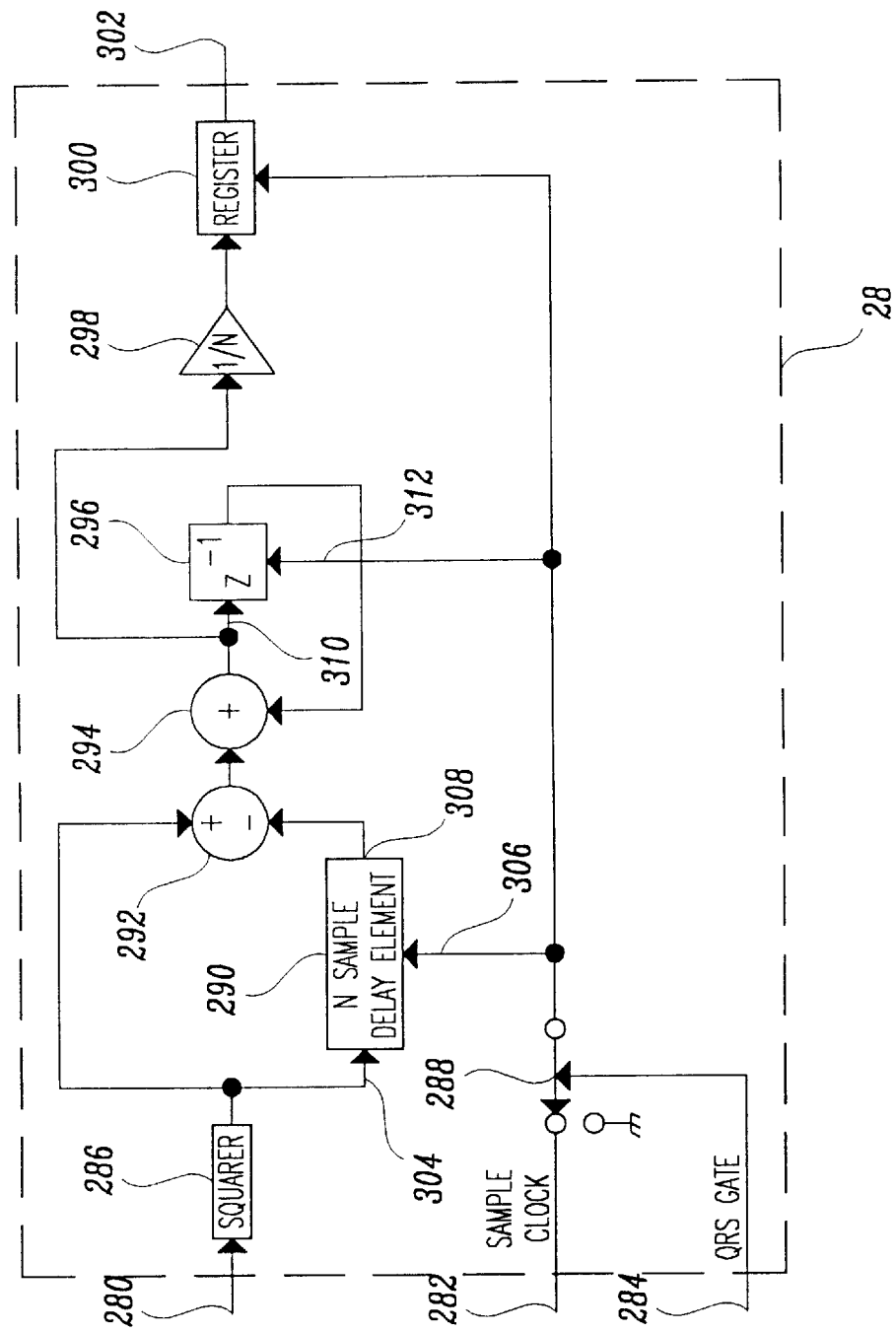
FIG. 15 is a detailed block diagram of the preferred form of the wideband noise detector of the present invention as shown from the block diagram of FIG. 1.

FIG. 15 is a block diagram of the preferred form of the wideband noise detector 28 shown in FIG. 1. The signal from the switch 38 is applied to the input 280 of the wideband noise detector 28. The signal at the input 280 is applied to the input of the squarer 286. The squarer 286 multiplies the signal by itself in order to obtain a value which is the square of the signal value at the input 280. The squared signal at the output of the squarer 286 is then presented simultaneously to the positive input of the summer 292 and to the input 304 of the N sample delay element 290.

The delay element 290 preferably imposes a time delay of N time units. A time unit is the period of the clock signal applied to the clock input 306. A signal appearing at the input 304 will appear at the output 308 after N clock pulses have occurred at the clock input 306. In the preferred embodiment, N=300 and the frequency of the clock signal at the clock input 306 is about 500 Hz. Therefore, the time unit would be about two milliseconds, and the time required for the signal to pass from the input 304 to the output 308 is about 600 milliseconds. If the clock signal at the clock input 306 stops, the signal value at the output 308 will remain at the current value until the next clock pulse occurs.

The delay element 290 consists of N electronic memory elements which store the most recent N samples of the signal appearing at the input 304. The sample value appearing at the output 308 is the oldest of the N samples. The delayed signal at the output of the delay element 290 is then presented to the negative input of the summer 292. The summer 292 subtracts the delayed signal at the output 308 of the delay element 290 from the signal at the output of the squarer 286. The resulting difference at the output of the summer 292 is then presented to the input of the summer 294.

The summer 294 and the unit delay 296 of the preferred form of the present invention form a digital integrator circuit. The summer 294 adds the signal at the output 314 of the unit delay 296 to the signal at the output of the summer 292. The resulting sum is presented to the input 310 of the unit delay 296. When a clock pulse occurs at the clock input 312 of the unit delay 296, the sum appearing on the input 310 of the unit delay 296 is transferred to the output 314 of the unit delay 296. In this way, every time a clock pulse occurs on the clock input 312, the value at the output 314 of the unit delay 296 is incremented by the value at the output of the summer 292. The value at the output 314 of the unit delay 296 is, therefore, the sum of all previous sampled values at the output of the summer 292.

The portion of the wideband noise detector 28 consisting of the N sample delay element 290, the summer 292, the summer 294, the unit delay 296 and the gain block 298 generally forms a sample averaging system. At any time, the signal at the output of the gain block 298 is a running average of the last N samples of the output of the squarer 286. Before beginning operation, the averaging system is reset by setting all of the memory elements of the delay element 290 to zero and setting the value in the unit delay 296 to zero. A new sample is included in the average when each clock pulse occurs.

For the first N samples after the system is reset, each sample value at the output of the squarer 286 is applied to the input of the summer 292. Because the output of the delay element 290 is zero, the output of the summer 292 has the same value as the output of the squarer 286. As described above, all these first N sample values are summed by an integrator consisting of the summer 294 and the unit delay 296. After N clock pulses have occurred, the output of the unit delay 296 contains the sum of the values of the first N samples. The output of the summer 294 is connected to the gain block 298, which multiplies the output of the sum of the values of the first N samples by the inverse of N. Therefore, the output of the gain block 298 contains the average of the first N samples.

After N clock pulses have occurred, the output of the delay element 290 contains the first (oldest) sample from the output of the squarer 286. Because the two summers are connected together, the output of the summer 294 now contains a value equal to the output of the squarer 286 plus the output of the unit delay 296 minus the output of the delay element 290. This means that, upon clock pulse N+1, the value of the oldest sample at the output 308 of the delay element 290 is subtracted from the sum currently in the unit delay 296, which was previously the sum of the first N samples including the sample now at the output of the delay element 290. In effect, the oldest sample is removed from the sum at the output 314 of the unit delay 296. Upon the next clock pulse (N+2), the second sample is removed from the sum at the output 314 of the unit delay 296. In the same manner, each time a clock pulse occurs, a new sample from the output of the squarer 286 is added to the sum in the unit delay 296, and the sample which was added N clock periods previous is removed from the sum in the unit delay 296. Thus, the output 314 of the unit delay 296 always contains the sum of the last N samples from the output of the squarer 286, and the output of the gain block 298 always contains the average of the last N samples from the output of the squarer 286.

The output of the gain block 298 is connected to the input of the register 300. When a clock pulse occurs, the value at the output of the gain block 298 is transferred to the output of the register 300. The output of the register 300 is also the output 302 of the wideband noise detector 28. As can be seen from the forgoing description, the output 302 of the wideband noise detector 28 contains the average of the most recent N squares of the samples of the signal at the input 280 of the wideband noise detector 28. This results in an estimate of the mean square value of the signal at the input 280.

The QRS gate signal from the input 29 of the noise detection system 10, after being stretched by pulse stretcher 30, is presented to the QRS gate input 284 of the wideband noise detector 28. The QRS gate signal at the input 284 is connected to the control input of the switch 288. The QRS gate is a logic signal which is high (true) during the QRS complex of the ECG signal. When the QRS gate signal is low (false), the switch 288 is in the position shown in FIG. 15 which connects the signal from the sample clock 282 to the clock inputs of the delay element 306, the unit delay 312 and the register 300 and allows operation of the wideband noise detector 28 as described above. During the QRS complex, the QRS gate signal is high. This causes the switch 288 to disconnect the sample clock from the delay element 306, the unit delay 312 and the register 300. In this condition, the last output value is held in the register 300 and presented at the output 302. The operation of the wideband noise detector is inhibited until the end of the QRS complex, when the QRS gate signal again goes low. The purpose of this behavior is to avoid measuring the portion of the ECG signal containing the QRS complex so that only noise between QRS complexes will be measured.

As shown in FIG. 1, the ECG signal at the input 14 is also applied directly to the baseline wander filter 16. The baseline estimate output 110 of the baseline wander filter 16 is an estimate of the baseline value of the ECG signal. The baseline estimate appearing at the output 110 is applied to the input 122 of the baseline wander detector 32. The baseline wander detector 32 produces a Boolean output 126 which indicates whether there is excessive baseline wander in the ECG signal as described below.

Figure 16:
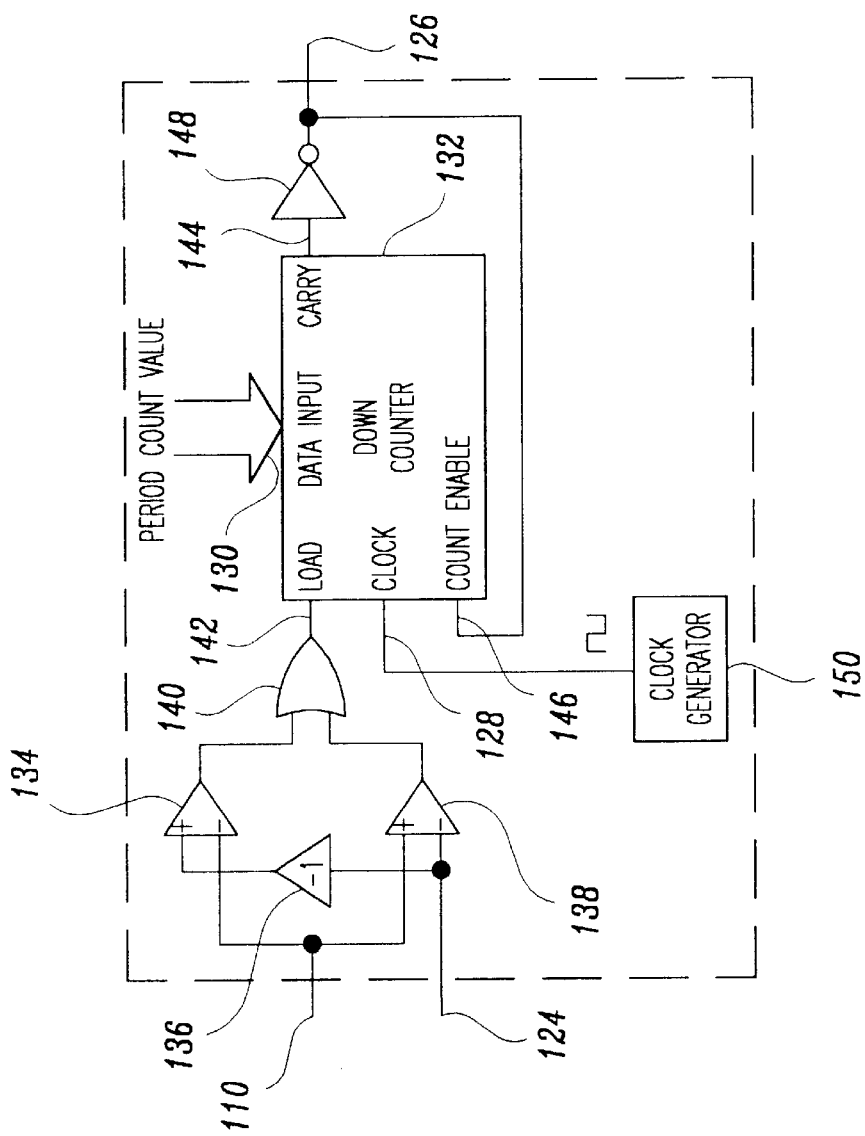
FIG. 16 is a block diagram of the preferred form of the baseline wander detector of the present invention as shown from the block diagram of FIG. 1.

FIG. 16 is a block diagram of a hardware realization of the preferred form of the baseline wander detector 32 of the present invention. The baseline wander estimate from the baseline wander estimate output 110 is applied to the baseline wander detector 32. If the amplitude of this baseline estimate exceeds the value of the baseline wander threshold presented at the input 124, then the Boolean baseline wander output 126 of the baseline wander detector 32 goes high (true), indicating the presence of excessive baseline wander in the ECG signal. If the baseline wander output 126 ever goes high, it will stay high for a certain period of time before being allowed to go low again in order to provide a stable and observable indication.

As shown in FIG. 16, the baseline wander estimate from the baseline wander estimate output 110 of the baseline wander filter 16 is applied to the baseline wander detector 32. This signal at the input 122 is presented simultaneously to the negative input of the comparator 134 and to the positive input of the comparator 138. The baseline wander threshold value is applied to the baseline wander detector 32 via the input 124. The threshold value at the input 124 is applied simultaneously to the negative input of the comparator 138 and to the input of a unity gain inverting amplifier 136. The output of the unity gain inverting amplifier 136 exhibits a signal which is the negative of the baseline wander threshold value at the input 124. The output of the inverting amplifier 136 is then applied to the positive input of the comparator 134. The outputs of the comparators 134 and 138 are presented to the inputs of the OR gate 140.

If the signal from the baseline wander estimate input 110 is greater than the baseline wander threshold value input 124, the output of the comparator 138 will go high and the output of the OR gate 140 will go high (true), indicating the existence of excessive baseline wander. Likewise, if the signal at the baseline wander detector 32 is less than the negative of the baseline wander threshold value input 124, the output of the comparator 134 will go high and the output of the OR gate 140 will go high (true), indicating the existence of excessive baseline wander. If the signal at the baseline wander detector 32 is less than the baseline wander threshold value at the input 124 and greater than the negative of the baseline wander threshold value at the input 124, then the outputs of the comparators 134 and 138 will both be low (false) and the output of the OR gate 140 will be low (false), indicating that the baseline wander in the ECG signal is not excessive.

The down counter 132 of the baseline wander detector 32 is preferably a binary down counter of a type well known in the art. In the preferred embodiment, this could be a 12-bit counter, having a maximum count value of about 4095. Changes at the control load input 142, the count enable input 146 and the data value input 130 have no effect until the rising edge of the clock input 128 occurs. The carry value output 144 of the down counter 132 will be high only when the internal value in the down counter 132 is 0. For all other internal count values, the carry value output 144 will be low. The clock generator 150 preferably produces a clock signal whose frequency is about 500 Hz. This frequency was chosen in the preferred embodiment because it is also the sample rate for the ECG data. The data value input 130 of the down counter 132 is permanently connected to a binary period count value. In the preferred embodiment, this value is preferably about 2000, which corresponds to a time period of approximately four seconds, because it would take about four seconds to count 2000 counts at approximately 500 counts per second. The 12-bit binary representation for the period count value 2000 is 011111010000.

The output of the OR gate 140 is connected to the load input 142 of the down counter 132. In the event that the absolute value of the baseline wander estimate value 110 exceeds the baseline wander threshold at the input of the baseline wander detector 32, the output of the OR gate 140 will be high to indicate the existence of excessive baseline wander. The control load input 142 of the down counter 132 will also be high. Because of the high logic level at the load input 142 of the down counter 132, when the next rising edge of the clock signal at the input 128 occurs, the period count value at the data input 130 will be loaded into the down counter 132. The carry output 144 is connected to the input of the inverter 148, and the output of the inverter 148 is connected to the baseline wander output 126 of the baseline wander detector 32. The baseline wander output 126 of the baseline wander detector 32 will therefore indicate the presence of excessive baseline wander. As long as the absolute value of the baseline estimate at the input 122 exceeds the baseline wander threshold at the input 124, the internal count value of the down counter 132 will remain at the period value of 2000 and the baseline wander output 126 will remain high.

When the absolute value of the baseline wander estimate value input becomes less than the baseline wander threshold 124, the load input 142 of the down counter 132 will go low. The output of the inverter 148 is connected to the count enable input 146 of the down counter 132. Because the carry output 144 is low, the count enable input 146 is high and counting is enabled. At the next rising edge of the clock signal at the clock input 128, the internal value of the down counter 132 will decrement to 1999. At each rising edge of the clock signal, the counter value will decrement once more. The baseline wander output 126 will remain high, however, until the counter value reaches zero. If the absolute value of the baseline estimate input 122 remains less than the value of the baseline wander threshold 124, for about four seconds or more, the internal value of the down counter 132 will decrement to zero. At this moment, the carry output 144 will go high, and the baseline wander output 126 will go low, indicating that excessive baseline wander is not present. Because the output of the inverter 148 is low and is also connected to the count enable input 146, the down counter 132 will be unable to change its internal value at subsequent clock transitions, and the internal count value will remain zero, and the baseline wander output 126 will remain low until such time as the baseline estimate input value 122 again becomes excessive.

As mentioned above, the instant invention is preferably implemented with a microprocessor. The following code fragment, written in the C language realizes baseline wander detector 32. The execution of this code fragment is preferably repeated at the clock rate of 500 times per second in the preferred embodiment although other clock rates could be employed if desired.

```
/* Detect baseline wander */
If (baseline_estimate > BASELINE_THRESHOLD
    || baseline_estimate < -BASELINE_THRESHOLD)
        baseline_counter = PERIOD_COUNT_VALUE;
Else
        if (baseline_counter > 0)
            --baseline_counter;
        if (baseline_counter ! = 0)
            baseline_wander = TRUE
```

The noise detection system of the present invention basically includes the steps of estimating noise levels, comparing the estimated noise levels to their respective noise threshold values and reporting the resulting noise statuses to the outside world.

As shown in FIG. 1, a comparator 40 compares the squared line noise estimate at the output of the line noise detector 24 with the line noise threshold presented at the signal input 52. Simultaneously, the comparator 42 compares the squared line noise estimate with 0.2 times the wideband noise power estimate. The outputs of the comparators 40 and 42 are ANDed together by AND gate 50. The result is that, if the line noise power estimate at the output of the line noise detector 24 is greater than the line noise threshold at the input 52 and also greater than 0.2 times the wideband noise power estimate, which is described below, the Boolean line noise status output 60 will be high (true), indicating that line noise is to be reported to the master. Because the output of the line noise detector 24 is in squared magnitude units, the line noise threshold presented to the input 52 must be the square of the desired noise threshold value.

The comparator 44 compares the wideband noise power estimate from the output of the wideband noise detector 28 with the wideband noise threshold presented at the input 56. The result of this comparison is that, if the wideband noise power estimate at the output of the wideband noise detector 28 is greater than the wideband noise threshold at the input 56, the Boolean wideband noise status output 54 will be high (true), indicating that wideband noise is to be reported to the master. Because the output of the wideband noise detector 28 is in squared magnitude units, the wideband noise threshold which is presented to the input 56 must be the square of the desired threshold value.

Likewise, the baseline wander detector 32 contains an internal comparator which compares the baseline estimate at the baseline wander output 110 of the baseline wander filter 16 with the baseline wander threshold presented at the input 62 of the ECG noise detection system 10. If the baseline wander estimate at the output 110 of the baseline wander filter 16 is greater than the baseline wander threshold presented to the input 62, the Boolean baseline wander status output 58 will be high (true), indicating that baseline wander is to be reported to the master. The noise statuses are represented as Boolean flags which are ORed into a status register that is sent to the master.

In order to determine numerical threshold values corresponding to the signal levels, the following formula is used:

$$L = S/Q$$

Where
- L is a numerical value representing a signal level.
- S is the signal level in expressed microvolts.
- Q is the quantization step size expressed in microvolts.

In the preferred embodiment of the instant invention, the quantization step size is about 1.0 microvolts. This is because the analog-to-digital conversion system that converts ECG signals to numerical values and presents these signals to the noise detection system produces one unit of change in numerical value in response to a voltage change of 1.0 microvolts at the input. Therefore, in the preferred embodiment, Q=1.0. Although this value of Q is used in the preferred embodiment, the instant invention may be readily adapted to work with other quantization step sizes as well.

An example will be given here to illustrate the calculation of the power line noise threshold. In the field of ECG acquisition and monitoring devices, it is desired to detect line noise signals greater than about 17 microvolts peak. Therefore, S=17 and Q=1. The value of L, the numerical representation of this signal level, according to the above equation, is 17. Because the line noise detector 24 produces an output equal to the square of one half the line noise amplitude, a line noise level of 17 microvolts would produce a line noise detector output equal to about 72.25. Therefore, the correct value for the line noise threshold at the input 52 of the noise detection system 10 would be about 72.

In summary, the preferred noise threshold values for the noise detection system 10 of the present invention are as follows. The preferred line noise threshold at the input 52 of the noise detection system 10 is equal to about 72, which represents a line noise amplitude of about 17 microvolts peak. The preferred wideband noise threshold presented at the input 56 of the noise detection system 10 is equal to about 200. The preferred baseline wander threshold that is presented to the input 62 of the noise detection system 10 is also equal to about 200, which represents a noise level of about 200 microvolts peak. When one or more of these preferred noise threshold values are reached, the monitoring system and user are preferably notified. If the monitoring system is configured to automatically begin the needed filtering, the displays and printouts will indicate that the filter is operative during the particular portion of the patient record. If the user does not want to perform filtering, the user may manually override the recommended filter, and the displays and prints will indicate the status of the respective filters.

I claim:

1. A device for detecting wide band noise from an ECG signal including a QRS portion received from a patient comprising:
    an ECG signal input for receiving the ECG signal including a QRS portion;
    an ECG gate circuit blanking said ECG signal from a point in time prior to an onset of the QRS portion of said ECG signal and ending at a point in time after an end of the QRS portion so that the QRS is removed;
    a high pass filter filtering said ECG signal to form a high pass filtered ECG signal with the QRS portion removed; and
    a wideband noise detector detecting a level of noise in said high pass filtered ECG signal with the QRS portion removed.

2. The device of claim 1 wherein said device further includes an adaptive line noise canceller removing line noise from said ECG signal, said adaptive line noise canceller being coupled between said ECG signal input and said high pass filter.

3. The device of claim 1 wherein said ECG gate circuit further includes an ECG gate signal derived from said ECG signal and a switch means responsive to said ECG gate signal for preventing the QRS portion of said ECG signal from being detected by said wideband noise detector.

4. The device of claim 1 wherein said device further includes a baseline wander filter to remove baseline wander from said ECG signal prior to said wideband noise detector.

5. The device of claim 1 wherein said high pass filter allows ECG signal frequencies above about 40 Hz to pass therethrough.

6. The device of claim 1 wherein said wideband noise detector has an output producing an indication signal that is an estimate of the amount of high frequency energy in said ECG signal.

7. A device for detecting muscle artifact noise in an ECG signal comprising:
    an ECG signal input for receiving an ECG signal having a QRS portion from a patient;
    an ECG gate signal derived from said ECG signal, said ECG gate signal beginning prior to an onset of the QRS portion of said ECG signal and ending at a point in time after the end of the QRS portion;
    means, connected to said input, for attenuating and delaying predetermined frequency components of said ECG signal to filter said ECG signal;
    switch means for allowing for the selective passage of said ECG signal therethrough in response to said ECG gate signal; and
    detector means, connected selectively through said switch means to said means for attenuating and delaying, for measuring wideband noise of said ECG signal which passes selectively through said switch means.

8. The device of claim 7 further including visual indication means responsive to said detector means for an indication to operator of the device that wideband noise exists in said ECG signal.

9. The device of claim 7 wherein said detector means further includes a wideband noise detector circuit and said wide band noise detector circuit includes a signal averaging system therein.

10. The device of claim 7 further including a means connected to said switch means for stretching said ECG gate signal timewise to lengthen the time said switch means allows such selective passage.

11. The device of claim 7 further including a wideband noise detector curcuit and means for inhibiting the operation of said wideband noise detector circuit while said switch means allows such selective passage.

12. A device for detecting noise from an ECG signal comprising:
    an ECG signal input for receiving an ECG signal from a patient;
    an ECG gate signal for blanking a portion of said ECG signal from a point in time prior to the onset of the QRS portion of said ECG signal and ending at a point in time after the end of the QRS portion;
    a switch member connected to said ECG input for allowing said ECG signal to selectively pass therethrough and blanking said ECG signal in response to said ECG gate signal; and
    a wideband noise detector for measuring wideband noise from said ECG signal having the QRS portion blanked wherein said wideband noise detector receives said ECG signal through said switch member.

13. The device of claim 12 wherein said switch member inhibits the passage of said ECG signal through said wideband noise detector.

14. The device of claim 12 wherein said switch member inhibits the passage of said ECG signal through said wideband noise detector during the QRS portion of said ECG signal.

15. The device of claim 12 further including a high pass filter to allow the high frequency portion of said ECG signal to pass therethrough and to said wideband noise detector.

16. The device of claim 12 further including an adaptive line noise canceler therein having a high pass filter therein to filter said ECG signal prior to said wideband noise detector.

17. A method for detecting noise from an ECG signal comprising:

providing an ECG signal input for receiving an ECG signal from a patient;

providing an ECG gate signal for blanking a portion of said ECG signal from a point in time prior to the onset of the QRS portion of said ECG signal and ending at a point in time after the end of the QRS portion;

providing the ECG signal and ECG gate signal to a switch member which is selectively opened and closed in response to said ECG gate signal to selectively allow said ECG signal to pass therethrough;

providing a wideband noise detector to measure the high frequency noise in the ECG signal following the switch member.

18. The method of claim 17 wherein the wideband noise detector measures the high frequency noise in the ECG signal after removing a QRS portion of the ECG signal.

19. The method of claim 17 wherein the ECG signal is filtered with a high pass filter following the switch member to allow the portion of the ECG signal having energy greater than 40 Hz to be presented to wideband noise detector.

* * * * *

UNITED STATES PATENT AND TRADEMARK OFFICE
CERTIFICATE OF CORRECTION

PATENT NO. : 5,999,845
DATED : December 7, 1999
INVENTOR(S) : Victor M. dePinto

It is certified that error appears in the above-indentified patent and that said Letters Patent is hereby corrected as shown below:

Claim 8, line 35, after "to" insert --an--.

Claim 13, line 66, before "inhibits" insert --selectively--.

Signed and Sealed this

Twenty-ninth Day of August, 2000

Attest:

Q. TODD DICKINSON

Attesting Officer

Director of Patents and Trademarks